US010344292B2

(12) United States Patent
Wagner et al.

(10) Patent No.: US 10,344,292 B2
(45) Date of Patent: Jul. 9, 2019

(54) SOYBEAN TRANSGENIC EVENT MON87705 AND METHODS FOR DETECTION THEREOF

(71) Applicant: Monsanto Technology LLC, St. Louis, MO (US)

(72) Inventors: Nicholas Wagner, Sacramento, CA (US); Wen C. Burns, Chesterfield, MO (US); Eric J. Godsy, Millstadt, IL (US); Peter D. Roberts, Benicia, CA (US)

(73) Assignee: Monsanto Technology LLC, St. Louis, MO (US)

( * ) Notice: Subject to any disclaimer, the term of this patent is extended or adjusted under 35 U.S.C. 154(b) by 157 days.

(21) Appl. No.: 15/403,854

(22) Filed: Jan. 11, 2017

(65) Prior Publication Data

US 2017/0112083 A1 Apr. 27, 2017

Related U.S. Application Data

(62) Division of application No. 13/930,925, filed on Jun. 28, 2013, now Pat. No. 9,572,311, which is a division of application No. 13/670,136, filed on Nov. 6, 2012, now Pat. No. 8,692,080, which is a division of application No. 12/568,321, filed on Sep. 28, 2009, now Pat. No. 8,329,989.

(60) Provisional application No. 61/100,859, filed on Sep. 29, 2008.

(51) Int. Cl.

| | |
|---|---|
| ***C12N 15/82*** | (2006.01) |
| ***C12Q 1/6895*** | (2018.01) |
| ***C12N 15/11*** | (2006.01) |
| *A23D 9/00* | (2006.01) |
| *C07H 21/04* | (2006.01) |
| *A23K 50/80* | (2016.01) |
| *A23L 11/00* | (2016.01) |

(52) U.S. Cl.

CPC .......... *C12N 15/8247* (2013.01); *C12N 15/11* (2013.01); *C12Q 1/6895* (2013.01); *A23D 9/00* (2013.01); *A23K 50/80* (2016.05); *A23L 11/00* (2016.08); *C07H 21/04* (2013.01); *C12Q 2600/13* (2013.01); *C12Q 2600/156* (2013.01); *Y02A 40/818* (2018.01)

(58) Field of Classification Search

None

See application file for complete search history.

(56) References Cited

U.S. PATENT DOCUMENTS

| | | | |
|---|---|---|---|
| 4,557,734 | A | 12/1985 | Schwab et al. |
| 5,454,842 | A | 10/1995 | Poirier et al. |
| 5,475,099 | A | 12/1995 | Knauf et al. |
| 5,500,361 | A | 3/1996 | Kinney |
| 5,627,061 | A | 5/1997 | Barry et al. |
| 5,633,435 | A | 5/1997 | Barry et al. |
| 5,714,670 | A | 2/1998 | Fehr et al. |
| 5,723,595 | A | 3/1998 | Thompson et al. |
| 5,723,761 | A | 3/1998 | Voelker et al. |
| 5,850,026 | A | 12/1998 | Debonte et al. |
| 5,888,947 | A | 3/1999 | Lambert et al. |
| 5,891,203 | A | 4/1999 | Ball et al. |
| 5,955,329 | A | 9/1999 | Yuan et al. |
| 5,955,650 | A | 9/1999 | Hitz |
| 6,013,114 | A | 1/2000 | Hille et al. |
| 6,150,512 | A | 11/2000 | Yuan |
| 6,331,664 | B1 | 12/2001 | Rubin-Wilson et al. |
| 6,369,296 | B1 | 4/2002 | Ratcliff et al. |
| 6,372,965 | B1 | 4/2002 | Lightner et al. |
| 6,380,462 | B1 | 4/2002 | Kridl |
| 6,384,301 | B1 | 5/2002 | Martinell et al. |
| 6,506,559 | B1 | 1/2003 | Fire et al. |
| 6,573,099 | B2 | 6/2003 | Graham |
| 7,166,771 | B2 | 1/2007 | Eenennaam et al. |
| 7,566,813 | B2 | 7/2009 | Voelker et al. |
| 7,601,888 | B2 | 10/2009 | Fillatti et al. |
| 2002/0034814 | A1 | 3/2002 | Atabekov et al. |
| 2003/0049835 | A1 | 3/2003 | Helliwell et al. |
| 2003/0135882 | A1 | 7/2003 | Metzlaff et al. |

(Continued)

FOREIGN PATENT DOCUMENTS

| | | | |
|---|---|---|---|
| AU | 200321427 | A1 | 10/2003 |
| AU | 2004276819 | B2 | 4/2005 |

(Continued)

OTHER PUBLICATIONS

Anklam et al., "Analytical methods for detection and determination of genetically modified organisms in agricultural crops and plant-derived food products," *Eur Food Res Technol*, 214:3-26 (2002).

(Continued)

*Primary Examiner* — Elizabeth F McElwain

(74) *Attorney, Agent, or Firm* — Arnold & Porter Kaye Scholer; Chunping Li; David Marsh

(57) ABSTRACT

The present invention provides a transgenic soybean event MON87705, and cells, seeds, and plants comprising DNA diagnostic for the soybean event. The invention also provides compositions comprising nucleotide sequences that are diagnostic for said soybean event in a sample, methods for detecting the presence of said soybean event nucleotide sequences in a sample, probes and primers for use in detecting nucleotide sequences that are diagnostic for the presence of said soybean event in a sample, growing the seeds of such soybean event into soybean plants, and breeding to produce soybean plants comprising DNA diagnostic for the soybean event.

17 Claims, 2 Drawing Sheets

Specification includes a Sequence Listing.

(56) References Cited

U.S. PATENT DOCUMENTS

| | | | |
|---|---|---|---|
| 2003/0172399 | A1 | 9/2003 | Fillatti |
| 2004/0006792 | A1 | 1/2004 | Fillatti et al. |
| 2004/0107459 | A1 | 6/2004 | Lardizabal et al. |
| 2004/0107460 | A1 | 6/2004 | Fillatti et al. |
| 2004/0126845 | A1 | 7/2004 | Eenennaam et al. |
| 2005/0034190 | A9 | 2/2005 | Fillatti et al. |
| 2006/0080750 | A1 | 4/2006 | Fillatti et al. |
| 2006/0206963 | A1 | 9/2006 | Voelker et al. |
| 2007/0074305 | A1 | 3/2007 | Eenennaam et al. |
| 2007/0214516 | A1 | 9/2007 | Fillatti et al. |
| 2008/0066201 | A1 | 3/2008 | Abad et al. |
| 2008/0222756 | A1 | 9/2008 | Fillatti et al. |
| 2009/0119805 | A1 | 5/2009 | Fillatti et al. |
| 2009/0151029 | A1 | 6/2009 | Voelker et al. |

FOREIGN PATENT DOCUMENTS

| | | | |
|---|---|---|---|
| AU | 2007215181 | A2 | 8/2007 |
| BR | PI 0414743-0 | A | 11/2006 |
| CA | 2 479 587 | A1 | 10/2003 |
| CA | 2 540 049 | A1 | 4/2005 |
| CA | 2 641 264 | A1 | 8/2007 |
| CN | 1655669 | A | 8/2005 |
| CN | 1886042 | A | 12/2006 |
| CN | 101421406 | A | 4/2009 |
| EP | 0 959 133 | A1 | 11/1999 |
| EP | 1 484 959 | A | 12/2004 |
| EP | 1 670 307 | A | 6/2006 |
| EP | 1 984 508 | A | 10/2008 |
| IN | 2255/DELNP/2006 | | 7/2007 |
| IN | 1430/CHENP/2008 | | 11/2008 |
| IN | 228211 | | 1/2009 |
| KR | 1020060063997 | A | 6/2006 |
| KR | 1020080009243 | A | 1/2008 |
| MX | PA04009134 | A | 1/2005 |
| WO | WO 93/11245 | A1 | 6/1993 |
| WO | WO 94/10189 | A1 | 5/1994 |
| WO | WO 94/11516 | A1 | 5/1994 |
| WO | WO 96/06936 | A1 | 3/1996 |
| WO | WO 98/05770 | A2 | 2/1998 |
| WO | WO 98/30083 | A1 | 7/1998 |
| WO | WO 98/46776 | A2 | 10/1998 |
| WO | WO 98/53083 | A1 | 11/1998 |
| WO | WO 98/56239 | A1 | 12/1998 |
| WO | WO 99/15682 | A2 | 4/1999 |
| WO | WO 99/32619 | A1 | 7/1999 |
| WO | WO 99/49029 | A1 | 9/1999 |
| WO | WO 99/53050 | A1 | 10/1999 |
| WO | WO 99/61631 | A1 | 12/1999 |
| WO | WO 99/64579 | A2 | 12/1999 |
| WO | WO 00/07432 | A1 | 2/2000 |
| WO | WO 00/18880 | A2 | 4/2000 |
| WO | WO 00/44895 | A1 | 8/2000 |
| WO | WO 00/44914 | A1 | 8/2000 |
| WO | WO 00/68374 | A1 | 11/2000 |
| WO | WO 01/11061 | A2 | 2/2001 |
| WO | WO 01/14538 | A2 | 3/2001 |
| WO | WO 01/34822 | A2 | 5/2001 |
| WO | WO 01/35726 | A1 | 5/2001 |
| WO | WO 01/36598 | A1 | 5/2001 |
| WO | WO 01/70949 | A1 | 9/2001 |
| WO | WO 01/79499 | A1 | 10/2001 |
| WO | WO 02/04581 | A1 | 1/2002 |
| WO | WO 02/15675 | A1 | 2/2002 |
| WO | WO 02/059336 | A2 | 8/2002 |
| WO | WO 02/081711 | A1 | 10/2002 |
| WO | WO 02/088301 | A2 | 11/2002 |
| WO | WO 03/080802 | A2 | 10/2003 |
| WO | WO 2004/000871 | A2 | 12/2003 |
| WO | WO 2004/001000 | A2 | 12/2003 |
| WO | WO 2004/001001 | A2 | 12/2003 |
| WO | 2004/009761 | | 1/2004 |
| WO | WO 2005/030982 | A2 | 4/2005 |
| WO | WO 2007/095243 | A2 | 8/2007 |
| WO | WO 2007/106728 | A2 | 9/2007 |

OTHER PUBLICATIONS

Anonymous, "Soybeans A3525," *Asgrow*, pp. 1-2(2004).

Ayele et al., "Whole genome shotgun sequencing of *Brassica oleracea* and its application to gene discovery and annotation in *Arabidopsis*," *Genome Research*, 15(4):487-495 (2005).

Bosher et al., "RNA Interference Can Target Pre-mRNA: Consequences for Gene Expression in a *Caenorhabditis elegans* Operon," *Genetics*, 153:1245-1256 (1999).

Bouchon et al., "Oil Distribution in Fried Potatoes Monitored by Infrared Microspectroscopy," *Journal of Food Science*, 66(7):918-923 (2001).

Brace, "Agronomic and seed traits of soybean lines with high-oleate concentration," *Graduate Theses and Dissertations*, Paper 11844 (2010).

Buhr et al., "Ribozyme Termination of RNA Transcripts Down-Regulate Seed Fatty Acid Genes in Transgenic Soybean," *The Plant Journal*, 30(2):155-163 (2002).

Burch-Smith et al., "Applications and advantages of virus-induced gene silencing for gene function studies in plants," *The Plant Journal*, 39:734-746(2004).

Cartea et al., "Comparison of Sense and Antisense Methodologies for Modifying the Fatty Acid Composition of *Arabidopsis thaliana* Oilseed," *Plant Science*, 136:181-194 (1998).

Chapman et al., "Transgenic cotton plants with increased seed oleic acid content," *JAOCS*, 78:941-947 (2001).

Chuang et al., "Specific and Heritable Genetic Interference by Double-Stranded RNA in *Arabidopsis thaliana*," *PNAS*, 97(9):4985-4990 (2000).

Clark-Walker et al., "Location of Transcriptional Control Signals and Transfer RNA Sequences in *Torulopsis glabrata* Mitochondrial DNA," *EMBO* (*European Molecular Biology Organization*) *Journal*, 4(2):465-473 (1985).

Clemente et al., "Soybean Oil: Genetic Approaches for Modification of Functionality and Total Content," *Plant Physiology*, 151:1030-1040 (2009).

Cogoni, C. et al., "Post-Transcriptional Gene Silencing Across Kingdoms," *Curr. Opin. Gen. & Devel.*, 10(6):638-643 (2000).

Colliver et al., "Differential modification of flavonoid and isoflavonoid biosynthesis with an antisense chalcone synthase construct in transgenic *Lotus corniculatus*," *Plant Mol. Biol.*, 35:509-522 (1997).

Crossway, A. et al., "Integration of Foreign DNA Following Microinjection of Tobacco Mesophyll Protoplasts," *Mol. Gen. Genet.*, 202(2):179-185 (1986).

Database Accession No. p65U (Jun. 22, 2007) (3 pages).

Database EM_GSS 'Online! EMBL Heidelberg, Germany; AL063932, May 29, 1999, GENOSCOPE; "*Drosophila melanogaster* genome survey sequence TET3 end of BAC: BACR8010," abstract.

Database EM_GSS 'Online! EMBL Heidelberg, Germany; AL069706, May 29, 1999, GENOSCOPE: "*Drosophila melanogaster* genome survey sequence T7 end of BAC: BACR29B23," abstract.

Database EM_GSS 'Online! EMBL Heidelberg, Germany; AL071390, May 29, 1999, GENOSCOPE: "*Drosophila melanogaster* genome surface sequence TET3 end of BAC: BACR32MO5," abstract.

Database EM_GSS 'Online! EMBL Heidelberg, Germany; AL105179, Jul. 26, 1999, GENOSCOPE: "*Drosophila melanogaster* genome survey sequence T7 end of BAC: BACN13A12," abstract.

Database EM_GSS 'Online! EMBL Heidelberg, Germany; AL108811, Jul. 26, 1999, GENOSCOPE: "*Drosophila melanogaster* genome survey sequence SP6 end of BAC BACN37D10," abstract.

Database EM_NEW 'Online! EMBL Heidelberg, Germany; AB026636, May 7, 1999, Sato S. et al.: "*Arabidopsis thaliana* genomic DNA, chromosome 3, TAC clone: K14A17," abstract.

Database EMEST_PLN 'Online! EMBL Heidelberg, Germany; AW397948, Feb. 8, 2000, Shoemaker R. et al.: "Public soybean EST project," abstract.

Database EM-NEW 'Online! EMBL Heidelberg, Germany; AB022220, Jan. 15, 1999, Sato S. et al.: "*Arabidopsis thaliana* genomic DNA, chromosome 3, P1 clone: MLN21," abstract.

Database EMPLN 'Online! EMBL Heidelberg, Germany; AC004705, May 21, 1998, Lin X et al.: "Sequence and analysis of chromosome 2 of the plant *Arabidopsis thaliana*," abstract.

(56) References Cited

OTHER PUBLICATIONS

Database EMPLN 'Online! EMBL Heidelberg, Germany; AL161581, Mar. 15, 2000, Weichselgartner M. et al.: "*Arabidopsis thaliana* chromosome 4, contig fragment No. 77," abstract.
Daun, "Effect of Frost Damage on the Quality of Canola (*B. napus*)," *JAOCS*, 62(4):715-719 (1985).
DeLuca, "Molecular characterization of secondary metabolic pathways," *AgBiotech News and Information*, 5(6):225N-229N (1993).
Dörmann, P. et al., "Accumulation of Palmitate in *Arabidopsis* Mediated by the Acyl-Acyl Carrier Protein Thioesterase FATB1," *Plant Physiology*, 123:637-643 (2000).
Duffield, J. et al., "U.S. Biodiesel Development: New Markets for Conventional and Genetically Modified Agricultural Products," *Economic Research Service USDA*, pp. 1-31 (1998).
Dunn, R. et al., "Recent Advances in the Development of Alternative Diesel Fuel from Vegetable Oils and Animal Fats," *Recent Res. Devel. in Oil Chem.*, 1:31-56 (1997).
Erhan, S. et al., "Lubricant Basestocks from Vegetable Oils," *Industrial Crops and Products*, 11:277-282 (2000).
European Search Report dated Mar. 16, 2012, in European Patent Application No. 09816983.2.
Fire, A. et al., "Potent and Specific Genetic Interference by Double-Stranded RNA in *Caenorhabditis elegans," Nature*, 391:806-811 (1998).
"Food Standards: Australia, New Zealand, Supporting Document 1 (at Approval). Application A1049—Food Derived from Herbicide-Tolerant, High Oleic Acid Soybean Line MON87705. Safety Assessment Report." XP55174211, 38 pages.
GenBank Accession No. BF324940, EST name su29c08.y1 (Jul. 13, 2004) (2 pages).
GenBank Accession No. BH684437, GSS name BOHXS88TR (Feb. 19, 2002) (2 pages).
Halpin, C. et al., "Enabling Technologies for Manipulating Multiple Genes on Complex Pathways," *Plant Molecular Biology*, 47:295-310 (2001).
Hamada, T. et al., "Modification of Fatty Acid Composition by Over- and Antisense-Expression of a Microsomal ω-3 Fatty Acid Desaturase Gene in Transgenic Tobacco," *Transgenic Research*, 5(2), 115-121 (1996).
Hamilton et al., "A Transgene with Repeated DNA Causes High Frequency, Post-Transcriptional Suppression of ACC-Oxidase Gene Expression in Tomato," *The Plant Journal*, 15(6):737-746 (1998).
Hoist-Jensen et al., "PCR technology for screening and quantification of genetically modified organisms (GMOs)," *Anal Bioanal Chem*, 375(8):985-993 (2003).
International Preliminary Examination Report in PCT/US00/22613 (published as WO 01/14538), dated Dec. 6, 2001.
International Preliminary Examination Report in PCT/US03/08610 (published as WO 03/080802), dated Mar. 4, 2004.
International Preliminary Examination Report in PCT/US03/19437 (published as WO 2004/001000), dated Jul. 27, 2004.
International Preliminary Examination Report in PCT/US03/19445 (published as WO 2004/001001), dated Nov. 4, 2004.
International Preliminary Report on Patentability in PCT/US2004/31605 (published as WO 2005/030982), dated Mar. 27, 2006.
International Preliminary Report on Patentability in PCT/US2007/003823 (published as WO 2007/095243), dated Aug. 19, 2008.
International Search Report in PCT/US00/22613 (published as WO 01/14538), dated Apr. 26, 2001.
International Search Report in PCT/US03/08610 (published as WO 03/080802), dated Nov. 13, 2003.
International Search Report in PCT/US03/19437 (published as WO 2004/001000), dated Jun. 21, 2004.
International Search Report in PCT/US03/19445 (published asWO 2004/001001), dated Apr. 9, 2004.
International Search Report in PCT/US2004/31605 (published as WO 2005/030982), dated Jul. 12, 2005.
International Search Report in PCT/US2007/003823 (published as WO 2007/095243), dated Jul. 12, 2007.
International Search Report dated Dec. 30, 2009, in International Application No. PCT/US2009/58591.
Jaworski et al., "Industrial oils from transgenic plants," *Current Opinion in Plant Biology*, 6(2):178-184 (2003).
La, "Seed Protein, Oil, and Yield of Soybean Genotypes with High and Normal Oleic Acid Concentration," *A Thesis Presented to the Faculty of the Graduate School at the University of Missouri-Columbia*, pp. 1-80 (2013).
Lang et al., "Preparation and characterization of bio-diesels from various bio oils," *Bioresource Technology*, 80:53-62 (2001).
Lee et al., "Antisense Expression of the CK2 α-Subunit Gene in *Arabidopsis*. Effects on Light-Regulated Gene Expression and Plant Growth," *Plant Physiology*, 119:989-1000 (1999).
Levin et al., "Methods of Double-Stranded RNA-Mediated Gene Inactivation in *Arabidopsis* and Their Use to Define an Essential Gene in Methionine Biosynthesis," *Plant Mol. Biol.*, 44(6):759-775 (2000).
Lewin, B., "How Did Interrupted Genes Evolve?," *Genes*, $2^{nd}$ Edition, pp. 333-337 (1985).
Martin et al., "A comparison of Oleic Acid Metabolism n the Soybean (*Glycine max* [L.] Merr.) Genotypes Williams and A5, a mutant with decreased linoleic acid in the seed," *Plant Phys.*, 61:41-44 (1986).
Martinez-Rivas et al., "Oxygen-independent temperature regulation of the microsomal oleate desaturase (FAD2) activity in developing sunflower (*Helianthus annuus*) seeds," *Physiologia Plantarum*, 117:179-185 (2003).
Matzke, M.A. et al., "RNA-Based Silencing Strategies in Plants," *Curr. Opin. Gen. & Devel.*, 11(2):221-227 (2001).
McCormick et al, "Effect of Humidity on Heavy-Duty Transient Emissions from Diesel and Natural Gas Engines at High Altitude," *Journal of the Air & Waste Management Association*, 47:784-791 (1997).
Mensink, R. et al., "Effect of Dietary Fatty Acids on Serum Lipids and Lipoproteins: A Meta-Analysis of 27 Trials," *Arteriosclerosis and Thrombosis*, 12(8):911-919 (1992).
Montgomery, M.K. et al., "RNA as a Target of Double-Stranded RNA-Mediated Genetic Interference in *Caenorhabditis elegans," Proc. Natl. Acad. Sci. USA*, 95(26):15502-15507 (1998).
Napoli, C. et al., "Introduction of a Chimeric Chalcone Synthase Gene into Petunia Results in Reversible Co-Suppression of Homologous Genes in trans," *The Plant Cell*, 2:279-289 (1990).
NCBI GenBank: BH 684437.1, *Brassica oleracea* genomic clone BOHXS88TR BO_2_3_KB (2002).
Neff, W.E. et al., "Odor Significance of Undersirable Degradation Compounds in Heated Triolein and Trilinolein," *JAOCS*, 77(12):1303-1313 (2000).
Okuley, J., et al., "Arabidopsis FAD2 Gene Encodes the Enzyme That Is Essential for Polyunsaturated Lipid Synthesis," *The Plant Cell*, 6:147-158 (1994).
Padgette et al., "Development, Identification, and Characterization of a Glyphosate-Tolerant Soybean Line," *Crop Sci.*, 35(5):1451-1461 (1995).
Peele et al., "Silencing of a meristematic gene using geminivirus-derived vectors," *The Plant Journal*, 27(4):357-366 (2001).
Pokorný, "Flavor Chemistry of Deep Fat Frying in Oil," *Flavor Chemistry of Lipid Foods* (eds. Min & Smouse), Chapter 7, pp. 113-155, American Oil Chem. Soc., Champaign, IL (1989).
Qing, L., Thesis, "The Isolation and Characterisation of Fatty Acid Desaturase Genes in Cotton," University of Sydney, Australia, pp. ii-iv, 24-26, 121-123, 142, 167-168, 172-174, 179-181 (1998).
Search Report Completed on Dec. 23, 2013, in ROC (Taiwan) Patent Application No. 098132546.
Search Report completed on Sep. 12, 2014, in ROC (Taiwan) Patent Application No. 098132546.
Sharp, P.A., "RNA Interference—2001," *Genes & Development*, 15(5):485-490 (2001).
Sharp, P.A., "RNAi and Double-Strand RNA," *Genes & Development*, 13(2):139-141 (1999).
Singh et al., "Metabolic engineering of new fatty acids in plants," *Current Opinion in Plant Biology*, 8(2):197-203 (2005).

(56) References Cited

OTHER PUBLICATIONS

Singh et al., "Transgenic expression of a delta 12-epoxygenase gene in *Arabidopsis* seeds inhibits accumulation of linoleic acid," *Planta*, 212:872-879 (2001).
Smith et al., "Total silencing by intron-spliced hairpin RNAs," *Nature*, 407:319-320 (2000).
Spear, "Agronomic, seed traits and oleate stability of soybean lines containing the high-oleate transgene CP-305423-1 and the molecular characterization of the genomic region flanking the high-oleate transgene," *Graduate Theses and Dissertations*, Paper 12830 (2012).
Stam et al., "Post-transcriptional silencing of chalcone synthase in *Petunia* by inverted transgene repeats," *The Plant Journal* 12(1):63-82 (1997).
Stam et al., "The Silence of Genes in Transgenic Plants," *Annals of Botany*, 79:3-12 (1997).
Stoutjesdijk et al., "hpRNA-Mediated Targeting of the *Arabidopsis* FAD 2 Gene Gives Highly Efficient and Stable Silencing," *Plant Physiology*, 129:1723-1731 (2002).
Supplemental European Search Report in European Application No. 03 71 1656.3 completed Jun. 29, 2005.
Supplementary European Search Report European Application No. 04 78 5109 (dated Nov. 7, 2006).
Supplementary Partial European Search Report in Application No. 03 76 1158 dated Jan. 8, 2007.
Sweetlove et al., "Starch metabolism in tubers of transgenic potato (*Solanum tuberosum*) with increased ADPglycose pyrophosphorylase," *Biochem. J.*, 320:493-498 (1996).
Thomas et al., "Size constraints for targeting post-transcriptional gene silencing and for RNA-directed methylation in *Nicotiana benthamiana* using a potato virus X vector," *The Plant Journal* 25(4):417-25 (2001).
Timmons, J.S. et al., "Relationships Among Dietary Roasted Soybeans, Milk Components, and Spontaneous Oxidized Flavor of Milk", *Journal of Diary Science*, 84(11):2440-2449 (2001).
Toborek, M. et al., "Unsaturated Fatty Acids Selectively Induce an Inflammatory Environment in Human Endothelial Cells", *American Journal of Clinical Nutrition*, 75:119-125 (2002).
van der Krol, A. R. et al., "Flavonoid Genes in Petunia: Addition of a Limited Number of Gene Copies May Lead to a Suppression of Gene Expression", *The Plant Cell*, 2:291-299 (1990).
Voelker et al., *Annu Rev Plant Physiol Plant Mol Biol*, 52:335-361 (2001).
Warner, K. et al., "Effect of Oleic and Linoleic Acids on the Production of Deep-Fried Odor in Heated Triolein and Trilinolein", *Journal of Agricultural Food Chemical*, 49:899-905 (2001).
Waterhouse, P.M. et al., "Virus Resistance and Gene Silencing in Plants Can be Induced by Simultaneous Expression of Sense and Antisense RNA", *Proc. Natl. Acad. Sci. USA*, 95(23):13959-13964 (1998).
Wesley, S.V. et al., "Construct Design for Efficient, Effective and High-Throughput Gene Silencing in Plants", *The Plant Journal*, 27(6):581-590 (2001).
Yu et al., "RNA interference by expression of short-interfering RNAs and hairpin RNAs in mammalian cells", *Proc. Natl. Acad. Sci.*, 99(9):6047-6052 (2002).
Genbank Accession No. AJ286132, (2001).
Kumar et al., "Gene Stability in transgenic aspen (Populus). II. Molecular characterization of variable expression of transgene in wild and hybrid aspen," *Planta*, 213:731-740 (2001).

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: 5' Junction sequence

<400> SEQUENCE: 1

aagtttgtgg ttcatgtccg                                               20


<210> SEQ ID NO 2
<211> LENGTH: 20
<212> TYPE: DNA
<213> ORGANISM: Artificial Sequence
<220> FEATURE:
<223> OTHER INFORMATION: 3' Junction Sequence

<400> SEQUENCE: 2

tacaattgaa gagactcagg                                               20


<210> SEQ ID NO 3
<211> LENGTH: 3458
<212> TYPE: DNA
<213> ORGANISM: Glycine max
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1243)..(1243)
<223> OTHER INFORMATION: n is a, c, g, or t
<220> FEATURE:
<221> NAME/KEY: misc_feature
<222> LOCATION: (1522)..(1522)
<223> OTHER INFORMATION: n is a, c, g, or t

<400> SEQUENCE: 3

actatagggc acgcgtggtc gacggnccgg gctggtaaac ttaacaaagc cttatatgga      60

cttaaacaag cttccaaagc ttggtatgga aaactaagtt catttatttt ggaaaatggc     120

tttgnacatg gaatggtcga cacaacactc tttcctaaga attatgattc tcaattttta     180

ttagtacaag tgtatgtgga tgatatcatt tttggtgcta ctaatgaaat gctctatgaa     240

gatttttcta agttaatgca aactgagttt gaaatgagca tgatgggaga gctaaaattc     300
```

-continued

```
ttccttggac tgcaaataaa gcaaacaccc caaggcattt acattcatca gaccaagtat    360
gtgaaaaatt agttgaagaa gttcaacata agtgatgaaa aagagatgaa gacttttatg    420
catcccacta cacatcttgg actggatgag gaatcaatga aggtggacgt gactcaatac    480
aaagcaatga ttggatcact gctctatctt aatgcttcta ggccttatat aatttttagt    540
gttttattat gtgcaagatt ccaaaaggaa ccaagggaag ttcatttaac tgcagttaaa    600
cctatattct aatatttaat tagaactcat aaccttggtc ttatgcttaa gagaagagat    660
agtttcagac tcatgagcta ttgagatgtg gactatgttg gtgataaagt cgaaagaaaa    720
agtacaagng gaagttgtca ctttataggt ggcaacttag tcacttggat atggaagaag    780
tagggatcaa ctacattgtt cactgctgaa gtagaatgcg tgtcagtagc catggaggtt    840
accctcgaca ttgangaccc caagaaatag gttcaaagtt ttggaaatcc acagggtcag    900
agcacaagtg caagtttcaa gtatcaaggc agcaacgaag ctatatcgta ggtaggggag    960
tttagtggta ccaataatgc ccaaacaccc actggtggga ctcaaaatct acaaggggag   1020
agcagaatgt cttctacatc atcaatatcc aaaccaagat tctcaagacc gtgaaacaaa   1080
ggatctcagg gtgttgttat cactgcggtt tggcctttgg gccaaggcac tgttgtcctg   1140
aaaaaaatat gagagttgta atactcgcta aggatgagta gattaatgaa gacggggaga   1200
tcntaggatt aaaaaatgag aatgaggaag aatgtgagga agntttggag atggtttgct   1260
agcggatgga tttgtcagtt tgttccgcag gtgggctaac ccagcctcaa gcatgaagct   1320
taggtgagaa ttataggggc aagaggtgat aatcttgatt gacaataggg caagccacaa   1380
ctttatatcc aacaaattgg tacataaatt gggactcagc atagatccca caaagcccta   1440
ttatatgaga ttgggggata gtaaccgcaa atccactcaa ggatgttgta agaacttaaa   1500
aaatagttgg gagcttatac cntggtagga tatttctatc tatttaagtt gggaggagtg   1560
gacctaatta ttggagttgc ttagttggaa acattgggag aaattaaggt gaattggagg   1620
accctaagta tgtcttttgt ccaccaagat cagaatatgg tgatcaagga gatcttggtt   1680
tattgaagac aatgatcatt ttgagaacat tgcaaaaaat agttagcaag gaagttgaga   1740
tgatgttcat gttgtgggta attgaaagca actatgtgga acaaattgat ttaacaaaga   1800
accaagaaaa ttagttgtag caagtactga tagagtttgc tacagttttt caggacctaa   1860
gggtttacca ccatctagag aggttgatca caagattgca attaagtccg gggcatatcc   1920
agataatgtt aggccttatc gttacccccca cttacagaag aatgagataa aaactctagt   1980
ggttgagatg ttatgattgg ggattattag actaagcaat agctcctatt ctagcccagt   2040
aattttggta aaaaggaaag atggaagttg acgattatgt atggattatc aggctttaag   2100
taaggctaca gtcccagaca agttcctgat tcctgtcatg aaagagttgt tggatgagtt   2160
aaatggaccc atccacttct ctaaaataga tctaaaggca aggtatcacc aaatcagaat   2220
gcacaaacct accttcagaa ctcaccaagg acattatgaa tctccagtga tgccatttgg   2280
attaacaaac accccgacca cgttccaatg agctatgaat gccacactga aaccgttcct   2340
tcgtaggtat gtggtagtgt tctttgatga cattttggtc tatagtaagt cttgggaagc   2400
ccatttggat catttgagtt aggtgttggc caggttatta gaacattatt tcttcacaaa   2460
tgtttttaaa aaaaaatgta gttttggtca aattaaggcg ggttgcttag ggcacgttat   2520
ctctaaagaa ggagttttga tgaggccatt ttgtagtggc caatgcctaa aactcctaag   2580
tctttgagag ggtttttgga acttacaggt tattataaaa ggtccatttg caattatggg   2640
```

-continued

```
aagatagctc gcccattgat tgatctatta aagtaaggaa attttaagtg gaatgaggat   2700
agtattaagg cttccataca attacaacaa gctattacca caataccaac actatccatg   2760
cttgattttt caaaacaatt ctccatagaa tgtgatgcct cggggaaggg aattggagtt   2820
gttctaacac aagatagaaa gcaaattgct tatttcaaca aggcattaaa agatttgact   2880
ctttctaaat ctatgtatga aaaggaatca atggctcttg tcttagccat acaacattgg   2940
aggccttatc ttccggatta gaaatttact atatacattg accaaaaaag tttgagatat   3000
ctactagatc agcgaattac aactcaacca acaatattgg gtagccaagt tgctggggta   3060
tgagtttgac attgtgtata aggtgggggc ttcaaacaag gttgttgatg ctctatctag   3120
aagagatgaa gacaaagaat tgcagggcat ttctagacct ttctggaaag acataacaaa   3180
aattaatgaa gaagttcaga aggatcccgc gttggctaaa atccgagaag aattgaagga   3240
taatctagat tcacaccctc agtacaccct ggagtgtgac atattatact tcagagggag   3300
gttggtccta ttagcttctt cattgtggat tccaaagtta ctacaagaat tccagacttc   3360
tcttatggga gggcactcgg gtatttacat aacttataga agaatcactc aatcgcttta   3420
ttggatacca ataaagggag aaatcactaa gtttgtgg                           3458
```

<210> SEQ ID NO 4
<211> LENGTH: 2515
<212> TYPE: DNA
<213> ORGANISM: Glycine max

<400> SEQUENCE: 4

```
gagactcagg gtgttgttat cactgcggtt tggcctttgg gccaaggcac cgttgtcctg     60
aaaaaaatat gagagttgta atactcgcta aggatgagta gattaatgaa gacggggaga    120
tcataggatt aaaaaatgag aatgaggaag aatgtgagga agttttggag atggtttgct    180
agcggatgga tttgtcagtt tgttccgcag gtgggctaac ccagcctcaa gcatgaagct    240
taggtgagaa ttataggggc aagaggtgat aatcttgatt gacaataggg caagccacaa    300
ctttatatcc aacaaattgg tacataaatt gggactcagc atagatccca caaagcccta    360
ttatatgaga ttgggggata gtaaccgcaa atccactcaa ggatgttgta agaacttaaa    420
aaatagttgg gagcttatac catggtagga tatttctatc tatttaagtt gggaggagtg    480
gacctaatta ttggagttgc ttagttggaa acattgggag aaattaaggt gaattggagg    540
accctaagta tgtcttttgt ccaccaagat cagaatatgg tgatcaagga gatcttggtt    600
tattgaagac aatgatcatt ttgagaacat tgcaaaaaat agttagcaag gaagttgaga    660
tgatgttcat gttgtgggta attgaaagca actatgtgga acaaattgat ttaacaaaga    720
accaagaaaa ttagttgtag caagtactga tagagtttgc tacagttttt caggacctaa    780
gggtttacca ccatctagag aggttgatca caagattgca attaagtccg gggcatatcc    840
agataatgtt aggccttatc gttacccccca cttacagaag aatgagataa aaactctagt    900
ggttgagatg ttatgattgg ggattattag actaagcaat agctcctatt ctagcccagt    960
aattttggta aaaaggaaag atggaagttg acgattatgt atggattatc aggctttaag   1020
taaggctaca gtcccagaca agttcctgat tcctgtcatg aaagagttgt tggatgagtt   1080
aaatggaccc atccacttct ctaaaataga tctaaaggca aggtatcacc aaatcagaat   1140
gcacaaacct accttcagaa ctcaccaagg acattatgaa tctccagtga tgccatttgg   1200
attaacaaac accccgacca cgttccaatg agctatgaat gccacactga aaccgttcct   1260
tcgtaggtat gtggtagtgt tctttgatga cattttggtc tatagtaagt cttgggaagc   1320
```

```
ccatttggat catttgagtt aggtgttggc caggttatta gaacattatt tcttcacaaa   1380
tgtttttaaa aaaaaatgta gttttggtca aattaaggcg ggttgcttag ggcacgttat   1440
ctctaaagaa ggagttttga tgaggccatt ttgtagtggc caatgcctaa aactcctaag   1500
actttgagag ggtttttgga acttacaggt tattataaaa ggtccatttg caattatggg   1560
aagatagctc gcccattgat tgatctatta aagtaaggaa attttaagtg gaatgaggat   1620
agtattaagg cttccataca attacaacaa gctattacca caataccaac actatccatg   1680
cttgattttt caaaacaatt ctccatagaa tgtgatgcct cggggaaggg aattggagtt   1740
gttctaacac aagatagaaa gcaaattgct tatttcaaca aggcattaaa agatttgact   1800
ctttctaaat ctatgtatga aaaggaatca atggctcttg tcttagccat acaacattgg   1860
aggccttatc ttccggatta gaaatttact atatacattg accaaaaaag tttgagatat   1920
ctactagatc agcgaattac aactcaacca acaatattgg gtagccaagt tgctggggta   1980
tgagtttgac attgtgtata aggtgggggc ttcaaacaag gttgttgatg ctctatctag   2040
aagagatgaa gacaaagaat tgcagggcat ttctagacct ttctggaaag acataacaaa   2100
aattaatgaa gaagttcaga aggatcccgc gttggctaaa atccgagaag aattgaagga   2160
taatctagat tcacaccctc agtacaccct ggagtgtgac atattatact tcagagggag   2220
gttggtccta ttagcttctt cattgtggat tccaaagtta ctacaagaat tccagacttc   2280
tcttatggga gggcactcgg gtatttacat aacttataga agaatcactc aatcgcttta   2340
ttggatacca ataaagggag aaatcactaa gtttgtggtt gcgtgtcatg tgggccaaag   2400
aagtaaatat caagcatcct ctccagcagg tttactacaa cctttgccaa ttccaaatgc   2460
tatttgggaa gaaattagta tgaattttat tgtaggtatg ctaaaatcaa aaggg        2515
```

<210> SEQ ID NO 5
<211> LENGTH: 7251
<212> TYPE: DNA
<213> ORGANISM: Artificial Sequence
<220> FEATURE:
<223> OTHER INFORMATION: Inserted cassettes

<400> SEQUENCE: 5

```
ttcatgtccg ggaaatctac atggatcagc aatgagtatg atggtcaata tggagaaaaa     60
gaaagagtaa ttaccaattt tttttcaatt caaaaatgta gatgtccgca gcgttattat    120
aaaatgaaag tacattttga taaaacgaca aattacgatc cgtcgtattt ataggcgaaa    180
gcaataaaca aattattcta attcggaaat ctttatttcg acgtgtctac attcacgtcc    240
aaatgggggc ttagatgaga aacttcacga tcgatgcggc cgtcgagtgg aagctaattc    300
tcagtccaaa gcctcaacaa ggtcagggta cagagtctcc aaaccattag ccaaaagcta    360
caggagatca atgaagaatc ttcaatcaaa gtaaactact gttccagcac atgcatcatg    420
gtcagtaagt ttcagaaaaa gacatccacc gaagacttaa agttagtggg catctttgaa    480
agtaatcttg tcaacatcga gcagctggct tgtggggacc agacaaaaaa ggaatggtgc    540
agaattgtta ggcgcaccta ccaaaagcat ctttgccttt attgcaaaga taaagcagat    600
tcctctagta caagtgggga acaaaataac gtggaaaaga gctgtcctga cagcccactc    660
actaatgcgt atgacgaacg cagtgacgac cacaaaagaa ttagcttgag ctcaggattt    720
agcagcattc cagattgggt tcaatcaaca aggtacgagc catatcactt tattcaaatt    780
ggtatcgcca aaaccaagaa ggaactccca tcctcaaagg tttgtaagga agaattcgat    840
```

-continued

```
atcaagcttg atatcggaag tttctctctt gagggaggtt gctcgtggaa tgggacacat    900
atggttgtta taataaacca tttccattgt catgagattt tgaggttaat atatacttta    960
cttgttcatt attttatttg gtgtttgaat aaatgatata aatggctctt gataatctgc   1020
attcattgag atatcaaata tttactctag agaagagtgt catatagatt gatggtccac   1080
aatcaatgaa atttttggga gacgaacatg tataaccatt tgcttgaata accttaatta   1140
aaaggtgtga ttaaatgatg tttgtaacat gtagtactaa acattcataa aacacaacca   1200
acccaagagg tattgagtat tcacggctaa acaggggcat aatggtaatt taaagaatga   1260
tattatttta tgttaaaccc taacattggt ttcggattca acgctataaa taaaaccact   1320
ctcgttgctg attccattta tcgttcttat tgaccctagc cgctacacac ttttctgcga   1380
tatctctgag gtaagcgtta acgtaccctt agatcgttct ttttcttttt cgtctgctga   1440
tcgttgctca tattatttcg atgattgttg gattcgatgc tctttgttga ttgatcgttc   1500
tgaaaattct gatctgttgt ttagatttta tcgattgtta atatcaacgt ttcactgctt   1560
ctaaacgata atttattcat gaaactattt tcccattctg atcgatcttg ttttgagatt   1620
ttaatttgtt cgattgattg ttggttggtg gatctatata cgagtgaact tgttgatttg   1680
cgtatttaag atgtatgtcg atttgaattg tgattgggta attctggagt agcataacaa   1740
atccagtgtt cccttttttct aagggtaatt ctcggattgt ttgctttata tctcttgaaa   1800
ttgccgattt gattgaattt agctcgctta gctcagatga tagagcacca caatttttgt   1860
ggtagaaatc ggtttgactc cgatagcggc tttttactat gattgttttg tgttaaagat   1920
gattttcata atggttatat atgtctactg tttttattga ttcaatattt gattgttctt   1980
tttttgcag atttgttgac cagagatcta ccatggcgca agttagcaga atctgcaatg   2040
gtgtgcagaa cccatctctt atctccaatc tctcgaaatc cagtcaacgc aaatctccct   2100
tatcggtttc tctgaagacg cagcagcatc cacgagctta tccgatttcg tcgtcgtggg   2160
gattgaagaa gagtgggatg acgttaattg gctctgagct tcgtcctctt aaggtcatgt   2220
cttctgtttc cacggcgtgc atgcttcacg gtgcaagcag ccgtccagca actgctcgta   2280
agtcctctgg tctttctgga accgtccgta ttccaggtga caagtctatc tcccacaggt   2340
ccttcatgtt tggaggtctc gctagcggtg aaactcgtat caccggtctt ttggaaggtg   2400
aagatgttat caacactggt aaggctatgc aagctatggg tgccagaatc cgtaaggaag   2460
gtgatacttg gatcattgat ggtgttggta acggtggact ccttgctcct gaggctcctc   2520
tcgatttcgg taacgctgca actggttgcc gtttgactat gggtcttgtt ggtgtttacg   2580
atttcgatag cactttcatt ggtgacgctt ctctcactaa gcgtccaatg ggtcgtgtgt   2640
tgaacccact tcgcgaaatg ggtgtgcagg tgaagtctga agacggtgat cgtcttccag   2700
ttaccttgcg tggaccaaag actccaacgc caatcaccta cagggtacct atggcttccg   2760
ctcaagtgaa gtccgctgtt ctgcttgctg gtctcaacac cccaggtatc accactgtta   2820
tcgagccaat catgactcgt gaccacactg aaaagatgct tcaaggtttt ggtgctaacc   2880
ttaccgttga gactgatgct gacggtgtgc gtaccatccg tcttgaaggt cgtggtaagc   2940
tcaccggtca agtgattgat gttccaggtg atccatcctc tactgctttc ccattggttg   3000
ctgccttgct tgttccaggt tccgacgtca ccatccttaa cgttttgatg aacccaaccc   3060
gtactggtct catcttgact ctgcaggaaa tgggtgccga catcgaagtg atcaacccac   3120
gtcttgctgg tggagaagac gtggctgact tgcgtgttcg ttcttctact ttgaagggtg   3180
ttactgttcc agaagaccgt gctccttcta tgatcgacga gtatccaatt ctcgctgttg   3240
```

-continued

```
cagctgcatt cgctgaaggt gctaccgtta tgaacggttt ggaagaactc cgtgttaagg   3300
aaagcgaccg tctttctgct gtcgcaaacg gtctcaagct caacggtgtt gattgcgatg   3360
aaggtgagac ttctctcgtc gtgcgtggtc gtcctgacgg taagggtctc ggtaacgctt   3420
ctggagcagc tgtcgctacc cacctcgatc accgtatcgc tatgagcttc ctcgttatgg   3480
gtctcgtttc tgaaaaccct gttactgttg atgatgctac tatgatcgct actagcttcc   3540
cagagttcat ggatttgatg gctggtcttg gagctaagat cgaactctcc gacactaagg   3600
ctgcttgatg agctcaagaa ttcgagctcg gtaccggatc ctaagatctt aggatcctct   3660
agctagagct ttcgttcgta tcatcggttt cgacaacgtt cgtcaagttc aatgcatcag   3720
tttcattgcg cacacaccag aatcctactg agtttgagta ttatggcatt gggaaaactg   3780
tttttcttgt accatttgtt gtgcttgtaa tttactgtgt tttttattcg gttttcgcta   3840
tcgaactgtg aaatggaaat ggatggagaa gagttaatga atgatatggt ccttttgttc   3900
attctcaaat taatattatt tgttttttct cttatttgtt gtgtgttgaa tttgaaatta   3960
taagagatat gcaaacattt tgttttgagt aaaaatgtgt caaatcgtgg cctctaatga   4020
ccgaagttaa tatgaggagt aaaacacttg tagttgtacc attatgctta ttcactaggc   4080
aacaaatata ttttcagacc tagaaaagct gcaaatgtta ctgaatacaa gtatgtcctc   4140
ttgtgtttta gacatttatg aactttcctt tatgtaattt tccagaatcc ttgtcagatt   4200
ctaatcattg ctttataatt atagttatac tcatggattt gtagttgagt atgaaaatat   4260
tttttaatgc attttatgac ttgccaattg attgacaaca tgcatcaatc gacctgcagc   4320
cactcgaagc ggcccaaccc gggggcctat atggcccggt ccggcggccg cggtacggtc   4380
gactctagag gatccccggc aaaaacattt aatacgtatt atttaagaaa aaaatatgta   4440
ataatatatt tatattttaa tatctattct tatgtatttt ttaaaaatct attatatatt   4500
gatcaactaa aatattttta tatctacact tattttgcat ttttatcaat ttttcttgcgt   4560
tttttggcat atttaataat gactattctt taataatcaa tcattattct tacatggtac   4620
atattgttgg aaccatatga agtgtccatt gcatttgact atgtggatag tgttttgatc   4680
caggcctcca tttgccgctt attaattaat ttggtaacag tccgtactaa tcagttactt   4740
atccttcctc catcataatt aatcttggta gtctcgaatg ccacaacact gactagtctc   4800
ttggatcata agaaaaagcc aaggaacaaa agaagacaaa acacaatgag agtatccttt   4860
gcatagcaat gtctaagttc ataaaattca aacaaaaacg caatcacaca cagtggacat   4920
cacttatcca ctagctgatc aggatcgccg cgtcaagaaa aaaaaactgg accccaaaag   4980
ccatgcacaa caacacgtac tcacaaaggt gtcaatcgag cagcccaaaa cattcaccaa   5040
ctcaacccat catgagccca cacatttgtt gtttctaacc caacctcaaa ctcgtattct   5100
cttccgccac ctcatttttg tttatttcaa cacccgtcaa actgcatgcc accccgtggc   5160
caaatgtcca tgcatgttaa caagacctat gactataaat atctgcaatc tcggcccagg   5220
ttttcatcat caagaaccgg gtaccgagct cgagcctagg ggtaaattaa attgtgcctg   5280
catctcggga tatttcatgt ggggttcatc atatttgttg aggaaaagaa actcccgaaa   5340
ttgaattatg catttatata tcctttttca tttctagatt tcctgaaggc ttaggtgtag   5400
gcacctagct agtagctaca atatcagcac ttctctctat tgataaacaa ttggctgtaa   5460
tgccgcagta gaggacgatc acaacatttc gtgctggtta ctttttgttt tatggtcatg   5520
atttcaagac tagacgttct accggagaag cgaccttaga aattcattat ggtggcaaca   5580
```

-continued

```
gctgctactt catcattttt ccctgttact tcaccctcgc cggactctgg tggagcaggc   5640

agcaaacttg gtggtgggcc tgcaaacctt ggaggactaa aatccaaatc tgcgtcttct   5700

ggtggcttga aggcaaaggc gcaagcccct tcgaaaatta atggaaccac agttgttaca   5760

tctaaagaaa gcttcaagca tgatgatgat ctaccttcgc ctccccccag aacttttatc   5820

aaccagtcct gcaggtttaa actatcagtg tttgaaaatg gcttcatgtc cgggaaatct   5880

acatggatca gcaaaggtag atcatcatca tgcttgaagc tttctttaga tgtaacaact   5940

gtggttccat taattttcga aggggcttgc gcctttgcct tcaagccacc agaagacgca   6000

gatttggatt ttagtcctcc aaggtttgca ggcccaccac caagtttgct gcctgctcca   6060

ccagagtccg gcgagggtga agtaacaggg aaaaatgatg aagtagcagc tgttgccacc   6120

ataatgaatt tctaaggtcg cttctccggt agaacgtcta gtcttgaaat catgaccata   6180

aaacaaaaag taaccagcac gaaatgttgt gatcgtcctc tactgcggca ttacagccaa   6240

ttgtttatca atagagagaa gtgctgatat tgtagctact agctaggtgc ctacacctaa   6300

gccttcagga aatctagaaa tgaaaaagga tatataaatg cataattcaa tttcgggagt   6360

ttcttttcct caacaaatat gatgaacccc acatgaaata tcccgagatg caggcacaat   6420

ttaatttacc cctaggacgc gtaacaaaag agtgcctcac atttgatgca atagctctgt   6480

aatgtttcat tcatttgctt atttcggcct tgtttttctc gtattctatg ggctgatgtc   6540

tcatatggga cttttctact agagagccta cgttacttta ccattatatt gtattctttg   6600

agacattatt attatttttt taccttttga ggacactctt tttttgtatt tgaaggaatt   6660

tattgtttat tttgtttgga atatgtttgg ttggatttat tcgattcata tatattatat   6720

aaaagtaatt atgttattaa gaaacgtagt aagaacttac aaatataagg atcgaatccc   6780

gaacttcatg caaatcaatt tacaacccac acaagtttaa cattaaatta acgtgattgg   6840

ttagtaaatt catgtttctc tgtttaattt gttgaatttg tacattataa gggcgaattc   6900

tgcagatatc catcacactg gcggccgcgg gtcccatata tatatagcga tcgcggcgcg   6960

ccaaatcgtg aagtttctca tctaagcccc catttggacg tgaatgtaga cacgtcgaaa   7020

taaagatttc cgaattagaa taatttgttt attgctttcg cctataaata cgacggatcg   7080

taatttgtcg ttttatcaaa atgtactttc attttataat aacgctgcgg acatctacat   7140

ttttgaattg aaaaaaaatt ggtaattact ctttcttttt ctccatattg accatcatac   7200

tcattgctga tccatgtaga tttcccggac atgaagccat ttacaattga a            7251
```

<210> SEQ ID NO 6
<211> LENGTH: 13224
<212> TYPE: DNA
<213> ORGANISM: Artificial Sequence
<220> FEATURE:
<223> OTHER INFORMATION: Contig
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t -continued
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1243)..(1243)
<223> OTHER INFORMATION: n is a, c, g, or t
<220> FEATURE:
<221> NAME/KEY: misc_feature
<222> LOCATION: (1522)..(1522)
<223> OTHER INFORMATION: n is a, c, g, or t

<400> SEQUENCE: 6

```
actatagggc acgcgtggtc gacggnccgg gctggtaaac ttaacaaagc cttatatgga     60

cttaaacaag cttccaaagc ttggtatgga aaactaagtt catttatttt ggaaaatggc    120

tttgnacatg gaatggtcga cacaacactc tttcctaaga attatgattc tcaattttta    180

ttagtacaag tgtatgtgga tgatatcatt tttggtgcta ctaatgaaat gctctatgaa    240

gatttttcta agttaatgca aactgagttt gaaatgagca tgatgggaga gctaaaattc    300

ttccttggac tgcaaataaa gcaaacaccc caaggcattt acattcatca gaccaagtat    360

gtgaaaaatt agttgaagaa gttcaacata agtgatgaaa aagagatgaa gacttttatg    420

catcccacta cacatcttgg actggatgag gaatcaatga aggtggacgt gactcaatac    480

aaagcaatga ttggatcact gctctatctt aatgcttcta ggccttatat aatttttagt    540

gttttattat gtgcaagatt ccaaaaggaa ccaagggaag ttcatttaac tgcagttaaa    600

cctatattct aatatttaat tagaactcat aaccttggtc ttatgcttaa gagaagagat    660

agtttcagac tcatgagcta ttgagatgtg gactatgttg gtgataaagt cgaaagaaaa    720

agtacaagng gaagttgtca ctttataggt ggcaacttag tcacttggat atggaagaag    780

tagggatcaa ctacattgtt cactgctgaa gtagaatgcg tgtcagtagc catggaggtt    840

accctcgaca ttgangaccc caagaaatag gttcaaagtt ttggaaatcc acagggtcag    900

agcacaagtg caagtttcaa gtatcaaggc agcaacgaag ctatatcgta ggtaggggag    960

tttagtggta ccaataatgc ccaaacaccc actggtggga ctcaaaatct acaaggggag   1020

agcagaatgt cttctacatc atcaatatcc aaaccaagat tctcaagacc gtgaaacaaa   1080

ggatctcagg gtgttgttat cactgcggtt tggcctttgg gccaaggcac tgttgtcctg   1140

aaaaaaatat gagagttgta atactcgcta aggatgagta gattaatgaa gacggggaga   1200

tcntaggatt aaaaaatgag aatgaggaag aatgtgagga agntttggag atggtttgct   1260

agcggatgga tttgtcagtt tgttccgcag gtgggctaac ccagcctcaa gcatgaagct   1320

taggtgagaa ttataggggc aagaggtgat aatcttgatt gacaataggg caagccacaa   1380

ctttatatcc aacaaattgg tacataaatt gggactcagc atagatccca caaagcccta   1440

ttatatgaga ttgggggata gtaaccgcaa atccactcaa ggatgttgta agaacttaaa   1500

aaatagttgg gagcttatac cntggtagga tatttctatc tatttaagtt gggaggagtg   1560

gacctaatta ttggagttgc ttagttggaa acattgggag aaattaaggt gaattggagg   1620

accctaagta tgtcttttgt ccaccaagat cagaatatgg tgatcaagga gatcttggtt   1680

tattgaagac aatgatcatt ttgagaacat tgcaaaaaat agttagcaag gaagttgaga   1740

tgatgttcat gttgtgggta attgaaagca actatgtgga acaaattgat ttaacaaaga   1800

accaagaaaa ttagttgtag caagtactga tagagtttgc tacagttttt caggacctaa   1860

gggtttacca ccatctagag aggttgatca caagattgca attaagtccg gggcatatcc   1920
```

-continued agataatgtt aggccttatc gttaccccca cttacagaag aatgagataa aaactctagt 1980
ggttgagatg ttatgattgg ggattattag actaagcaat agctcctatt ctagcccagt 2040
aattttggta aaaaggaaag atggaagttg acgattatgt atggattatc aggctttaag 2100
taaggctaca gtcccagaca agttcctgat tcctgtcatg aaagagttgt tggatgagtt 2160
aaatggaccc atccacttct ctaaaataga tctaaaggca aggtatcacc aaatcagaat 2220
gcacaaacct accttcagaa ctcaccaagg acattatgaa tctccagtga tgccatttgg 2280
attaacaaac accccgacca cgttccaatg agctatgaat gccacactga aaccgttcct 2340
tcgtaggtat gtggtagtgt tctttgatga cattttggtc tatagtaagt cttgggaagc 2400
ccatttggat catttgagtt aggtgttggc caggttatta gaacattatt tcttcacaaa 2460
tgtttttaaa aaaaaatgta gttttggtca aattaaggcg ggttgcttag ggcacgttat 2520
ctctaaagaa ggagttttga tgaggccatt ttgtagtggc caatgcctaa aactcctaag 2580
tctttgagag ggtttttgga acttacaggt tattataaaa ggtccatttg caattatggg 2640
aagatagctc gcccattgat tgatctatta aagtaaggaa attttaagtg gaatgaggat 2700
agtattaagg cttccataca attacaacaa gctattacca caataccaac actatccatg 2760
cttgattttt caaaacaatt ctccatagaa tgtgatgcct cggggaaggg aattggagtt 2820
gttctaacac aagatagaaa gcaaattgct tatttcaaca aggcattaaa agatttgact 2880
ctttctaaat ctatgtatga aaaggaatca atggctcttg tcttagccat acaacattgg 2940
aggccttatc ttccggatta gaaatttact atatacattg accaaaaaag tttgagatat 3000
ctactagatc agcgaattac aactcaacca acaatattgg gtagccaagt tgctggggta 3060
tgagtttgac attgtgtata aggtgggggc ttcaaacaag gttgttgatg ctctatctag 3120
aagagatgaa gacaaagaat tgcagggcat ttctagacct ttctggaaag acataacaaa 3180
aattaatgaa gaagttcaga aggatcccgc gttggctaaa atccgagaag aattgaagga 3240
taatctagat tcacaccctc agtacaccct ggagtgtgac atattatact tcagagggag 3300
gttggtccta ttagcttctt cattgtggat tccaaagtta ctacaagaat tccagacttc 3360
tcttatggga gggcactcgg gtatttacat aacttataga agaatcactc aatcgcttta 3420
ttggatacca ataaagggag aaatcactaa gtttgtggtt catgtccggg aaatctacat 3480
ggatcagcaa tgagtatgat ggtcaatatg gagaaaaaga aagagtaatt accaattttt 3540
tttcaattca aaaatgtaga tgtccgcagc gttattataa aatgaaagta cattttgata 3600
aaacgacaaa ttacgatccg tcgtatttat aggcgaaagc aataaacaaa ttattctaat 3660
tcggaaatct ttatttcgac gtgtctacat tcacgtccaa atgggggctt agatgagaaa 3720
cttcacgatc gatgcggccg tcgagtggaa gctaattctc agtccaaagc ctcaacaagg 3780
tcagggtaca gagtctccaa accattagcc aaaagctaca ggagatcaat gaagaatctt 3840
caatcaaagt aaactactgt tccagcacat gcatcatggt cagtaagttt cagaaaaaga 3900
catccaccga agacttaaag ttagtgggca tctttgaaag taatcttgtc aacatcgagc 3960
agctggcttg tggggaccag acaaaaaagg aatggtgcag aattgttagg cgcacctacc 4020
aaaagcatct ttgcctttat tgcaaagata aagcagattc ctctagtaca agtggggaac 4080
aaaataacgt ggaaaagagc tgtcctgaca gcccactcac taatgcgtat gacgaacgca 4140
gtgacgacca caaaagaatt agcttgagct caggatttag cagcattcca gattgggttc 4200
aatcaacaag gtacgagcca tatcacttta ttcaaattgg tatcgccaaa accaagaagg 4260
aactcccatc ctcaaaggtt tgtaaggaag aattcgatat caagcttgat atcggaagtt 4320

-continued

```
tctctcttga gggaggttgc tcgtggaatg ggacacatat ggttgttata ataaaccatt   4380
tccattgtca tgagattttg aggttaatat atactttact tgttcattat tttatttggt   4440
gtttgaataa atgatataaa tggctcttga taatctgcat tcattgagat atcaaatatt   4500
tactctagag aagagtgtca tatagattga tggtccacaa tcaatgaaat ttttgggaga   4560
cgaacatgta taaccatttg cttgaataac cttaattaaa aggtgtgatt aaatgatgtt   4620
tgtaacatgt agtactaaac attcataaaa cacaaccaac ccaagaggta ttgagtattc   4680
acggctaaac aggggcataa tggtaattta aagaatgata ttattttatg ttaaacccta   4740
acattggttt cggattcaac gctataaata aaaccactct cgttgctgat tccatttatc   4800
gttcttattg accctagccg ctacacactt ttctgcgata tctctgaggt aagcgttaac   4860
gtacccttag atcgttcttt ttctttttcg tctgctgatc gttgctcata ttatttcgat   4920
gattgttgga ttcgatgctc tttgttgatt gatcgttctg aaaattctga tctgttgttt   4980
agattttatc gattgttaat atcaacgttt cactgcttct aaacgataat ttattcatga   5040
aactattttc ccattctgat cgatcttgtt ttgagatttt aatttgttcg attgattgtt   5100
ggttggtgga tctatatacg agtgaacttg ttgatttgcg tatttaagat gtatgtcgat   5160
ttgaattgtg attgggtaat tctggagtag cataacaaat ccagtgttcc ctttttctaa   5220
gggtaattct cggattgttt gctttatatc tcttgaaatt gccgatttga ttgaatttag   5280
ctcgcttagc tcagatgata gagcaccaca atttttgtgg tagaaatcgg tttgactccg   5340
atagcggctt tttactatga ttgttttgtg ttaaagatga ttttcataat ggttatatat   5400
gtctactgtt tttattgatt caatatttga ttgttctttt ttttgcagat ttgttgacca   5460
gagatctacc atggcgcaag ttagcagaat ctgcaatggt gtgcagaacc catctcttat   5520
ctccaatctc tcgaaatcca gtcaacgcaa atctccctta tcggtttctc tgaagacgca   5580
gcagcatcca cgagcttatc cgatttcgtc gtcgtgggga ttgaagaaga gtgggatgac   5640
gttaattggc tctgagcttc gtcctcttaa ggtcatgtct tctgtttcca cggcgtgcat   5700
gcttcacggt gcaagcagcc gtccagcaac tgctcgtaag tcctctggtc tttctggaac   5760
cgtccgtatt ccaggtgaca agtctatctc ccacaggtcc ttcatgtttg gaggtctcgc   5820
tagcggtgaa actcgtatca ccggtctttt ggaaggtgaa gatgttatca acactggtaa   5880
ggctatgcaa gctatgggtg ccagaatccg taaggaaggt gatacttgga tcattgatgg   5940
tgttggtaac ggtggactcc ttgctcctga ggctcctctc gatttcggta acgctgcaac   6000
tggttgccgt ttgactatgg gtcttgttgg tgtttacgat ttcgatagca ctttcattgg   6060
tgacgcttct ctcactaagc gtccaatggg tcgtgtgttg aacccacttc gcgaaatggg   6120
tgtgcaggtg aagtctgaag acggtgatcg tcttccagtt accttgcgtg gaccaaagac   6180
tccaacgcca atcacctaca gggtacctat ggcttccgct caagtgaagt ccgctgttct   6240
gcttgctggt ctcaacaccc caggtatcac cactgttatc gagccaatca tgactcgtga   6300
ccacactgaa aagatgcttc aaggttttgg tgctaacctt accgttgaga ctgatgctga   6360
cggtgtgcgt accatccgtc ttgaaggtcg tggtaagctc accggtcaag tgattgatgt   6420
tccaggtgat ccatcctcta ctgctttccc attggttgct gccttgcttg ttccaggttc   6480
cgacgtcacc atccttaacg ttttgatgaa cccaacccgt actggtctca tcttgactct   6540
gcaggaaatg ggtgccgaca tcgaagtgat caacccacgt cttgctggtg gagaagacgt   6600
ggctgacttg cgtgttcgtt cttctacttt gaagggtgtt actgttccag aagaccgtgc   6660
```

-continued

```
tccttctatg atcgacgagt atccaattct cgctgttgca gctgcattcg ctgaaggtgc   6720
taccgttatg aacggtttgg aagaactccg tgttaaggaa agcgaccgtc tttctgctgt   6780
cgcaaacggt ctcaagctca acggtgttga ttgcgatgaa ggtgagactt ctctcgtcgt   6840
gcgtggtcgt cctgacggta agggtctcgg taacgcttct ggagcagctg tcgctaccca   6900
cctcgatcac cgtatcgcta tgagcttcct cgttatgggt ctcgtttctg aaaaccctgt   6960
tactgttgat gatgctacta tgatcgctac tagcttccca gagttcatgg atttgatggc   7020
tggtcttgga gctaagatcg aactctccga cactaaggct gcttgatgag ctcaagaatt   7080
cgagctcggt accggatcct aagatcttag gatcctctag ctagagcttt cgttcgtatc   7140
atcggtttcg acaacgttcg tcaagttcaa tgcatcagtt tcattgcgca cacaccagaa   7200
tcctactgag tttgagtatt atggcattgg gaaaactgtt tttcttgtac catttgttgt   7260
gcttgtaatt tactgtgttt tttattcggt tttcgctatc gaactgtgaa atggaaatgg   7320
atggagaaga gttaatgaat gatatggtcc ttttgttcat tctcaaatta atattatttg   7380
tttttctct tatttgttgt gtgttgaatt tgaaattata agagatatgc aaacattttg   7440
ttttgagtaa aaatgtgtca aatcgtggcc tctaatgacc gaagttaata tgaggagtaa   7500
aacacttgta gttgtaccat tatgcttatt cactaggcaa caaatatatt ttcagaccta   7560
gaaaagctgc aaatgttact gaatacaagt atgtcctctt gtgttttaga catttatgaa   7620
ctttccttta tgtaattttc cagaatcctt gtcagattct aatcattgct ttataattat   7680
agttatactc atggatttgt agttgagtat gaaaatattt tttaatgcat tttatgactt   7740
gccaattgat tgacaacatg catcaatcga cctgcagcca ctcgaagcgg cccaacccgg   7800
gggcctatat ggcccggtcc ggcggccgcg gtacggtcga ctctagagga tccccggcaa   7860
aaacatttaa tacgtattat ttaagaaaaa aatatgtaat aatatattta tattttaata   7920
tctattctta tgtatttttt aaaaatctat tatatattga tcaactaaaa tatttttata   7980
tctacactta ttttgcattt ttatcaattt tcttgcgttt tttggcatat ttaataatga   8040
ctattcttta ataatcaatc attattctta catggtacat attgttggaa ccatatgaag   8100
tgtccattgc atttgactat gtggatagtg ttttgatcca ggcctccatt tgccgcttat   8160
taattaattt ggtaacagtc cgtactaatc agttacttat ccttcctcca tcataattaa   8220
tcttggtagt ctcgaatgcc acaacactga ctagtctctt ggatcataag aaaaagccaa   8280
ggaacaaaag aagacaaaac acaatgagag tatcctttgc atagcaatgt ctaagttcat   8340
aaaattcaaa caaaaacgca atcacacaca gtggacatca cttatccact agctgatcag   8400
gatcgccgcg tcaagaaaaa aaaactggac cccaaaagcc atgcacaaca acacgtactc   8460
acaaaggtgt caatcgagca gcccaaaaca ttcaccaact caacccatca tgagcccaca   8520
catttgttgt ttctaaccca acctcaaact cgtattctct tccgccacct catttttgtt   8580
tatttcaaca cccgtcaaac tgcatgccac cccgtggcca aatgtccatg catgttaaca   8640
agacctatga ctataaatat ctgcaatctc ggcccaggtt ttcatcatca agaaccgggt   8700
accgagctcg agcctagggg taaattaaat tgtgcctgca tctcgggata tttcatgtgg   8760
ggttcatcat atttgttgag gaaaagaaac tcccgaaatt gaattatgca tttatatatc   8820
ctttttcatt tctagatttc ctgaaggctt aggtgtaggc acctagctag tagctacaat   8880
atcagcactt ctctctattg ataaacaatt ggctgtaatg ccgcagtaga ggacgatcac   8940
aacatttcgt gctggttact ttttgtttta tggtcatgat ttcaagacta gacgttctac   9000
cggagaagcg accttagaaa ttcattatgg tggcaacagc tgctacttca tcatttttcc   9060
```

-continued

```
ctgttacttc accctcgccg gactctggtg gagcaggcag caaacttggt ggtgggcctg   9120
caaaccttgg aggactaaaa tccaaatctg cgtcttctgg tggcttgaag gcaaaggcgc   9180
aagccccttc gaaaattaat ggaaccacag ttgttacatc taaagaaagc ttcaagcatg   9240
atgatgatct accttcgcct ccccccagaa cttttatcaa ccagtcctgc aggtttaaac   9300
tatcagtgtt tgaaaatggc ttcatgtccg ggaaatctac atggatcagc aaaggtagat   9360
catcatcatg cttgaagctt tctttagatg taacaactgt ggttccatta attttcgaag   9420
gggcttgcgc ctttgccttc aagccaccag aagacgcaga tttggatttt agtcctccaa   9480
ggtttgcagg cccaccacca agtttgctgc ctgctccacc agagtccggc gagggtgaag   9540
taacagggaa aaatgatgaa gtagcagctg ttgccaccat aatgaatttc taaggtcgct   9600
tctccggtag aacgtctagt cttgaaatca tgaccataaa acaaaaagta accagcacga   9660
aatgttgtga tcgtcctcta ctgcggcatt acagccaatt gtttatcaat agagagaagt   9720
gctgatattg tagctactag ctaggtgcct acacctaagc cttcaggaaa tctagaaatg   9780
aaaaaggata tataaatgca taattcaatt tcgggagttt cttttcctca acaaatatga   9840
tgaaccccac atgaaatatc ccgagatgca ggcacaattt aatttacccc taggacgcgt   9900
aacaaaagag tgcctcacat ttgatgcaat agctctgtaa tgtttcattc atttgcttat   9960
ttcggccttg tttttctcgt attctatggg ctgatgtctc atatgggact tttctactag  10020
agagcctacg ttactttacc attatattgt attctttgag acattattat tattttttta  10080
ccttttgagg acactctttt tttgtatttg aaggaattta ttgtttattt tgtttggaat  10140
atgtttggtt ggatttattc gattcatata tattatataa aagtaattat gttattaaga  10200
aacgtagtaa gaacttacaa atataaggat cgaatcccga acttcatgca aatcaattta  10260
caacccacac aagtttaaca ttaaattaac gtgattggtt agtaaattca tgtttctctg  10320
tttaatttgt tgaatttgta cattataagg gcgaattctg cagatatcca tcacactggc  10380
ggccgcgggt cccatatata tatagcgatc gcggcgcgcc aaatcgtgaa gtttctcatc  10440
taagccccca tttggacgtg aatgtagaca cgtcgaaata aagatttccg aattagaata  10500
atttgtttat tgctttcgcc tataaatacg acggatcgta atttgtcgtt ttatcaaaat  10560
gtactttcat tttataataa cgctgcggac atctacattt ttgaattgaa aaaaaattgg  10620
taattactct ttcttttttct ccatattgac catcatactc attgctgatc catgtagatt  10680
tcccggacat gaagccattt acaattgaag agactcaggg tgttgttatc actgcggttt  10740
ggcctttggg ccaaggcacc gttgtcctga aaaaaatatg agagttgtaa tactcgctaa  10800
ggatgagtag attaatgaag acggggagat cataggatta aaaaatgaga atgaggaaga  10860
atgtgaggaa gttttggaga tggtttgcta gcggatggat ttgtcagttt gttccgcagg  10920
tgggctaacc cagcctcaag catgaagctt aggtgagaat tataggggca agaggtgata  10980
atcttgattg acaatagggc aagccacaac tttatatcca acaaattggt acataaattg  11040
ggactcagca tagatcccac aaagccctat tatatgagat tgggggatag taaccgcaaa  11100
tccactcaag gatgttgtaa gaacttaaaa aatagttggg agcttatacc atggtaggat  11160
atttctatct atttaagttg ggaggagtgg acctaattat tggagttgct tagttggaaa  11220
cattgggaga aattaaggtg aattggagga ccctaagtat gtcttttgtc caccaagatc  11280
agaatatggt gatcaaggag atcttggttt attgaagaca atgatcattt tgagaacatt  11340
gcaaaaaata gttagcaagg aagttgagat gatgttcatg ttgtgggtaa ttgaaagcaa  11400
```

-continued

```
ctatgtggaa caaattgatt taacaaagaa ccaagaaaat tagttgtagc aagtactgat  11460

agagtttgct acagtttttc aggacctaag ggtttaccac catctagaga ggttgatcac  11520

aagattgcaa ttaagtccgg ggcatatcca gataatgtta ggccttatcg ttacccccac  11580

ttacagaaga atgagataaa aactctagtg gttgagatgt tatgattggg gattattaga  11640

ctaagcaata gctcctattc tagcccagta attttggtaa aaaggaaaga tggaagttga  11700

cgattatgta tggattatca ggctttaagt aaggctacag tcccagacaa gttcctgatt  11760

cctgtcatga aagagttgtt ggatgagtta aatggaccca tccacttctc taaaatagat  11820

ctaaaggcaa ggtatcacca aatcagaatg cacaaaccta ccttcagaac tcaccaagga  11880

cattatgaat ctccagtgat gccatttgga ttaacaaaca ccccgaccac gttccaatga  11940

gctatgaatg ccacactgaa accgttcctt cgtaggtatg tggtagtgtt ctttgatgac  12000

attttggtct atagtaagtc ttgggaagcc catttggatc atttgagtta ggtgttggcc  12060

aggttattag aacattattt cttcacaaat gtttttaaaa aaaaatgtag ttttggtcaa  12120

attaaggcgg gttgcttagg gcacgttatc tctaaagaag gagttttgat gaggccattt  12180

tgtagtggcc aatgcctaaa actcctaaga ctttgagagg gtttttggaa cttacaggtt  12240

attataaaag gtccatttgc aattatggga agatagctcg cccattgatt gatctattaa  12300

agtaaggaaa ttttaagtgg aatgaggata gtattaaggc ttccatacaa ttacaacaag  12360

ctattaccac aataccaaca ctatccatgc ttgatttttc aaaacaattc tccatagaat  12420

gtgatgcctc ggggaaggga attggagttg ttctaacaca agatagaaag caaattgctt  12480

atttcaacaa ggcattaaaa gatttgactc tttctaaatc tatgtatgaa aaggaatcaa  12540

tggctcttgt cttagccata caacattgga ggccttatct tccggattag aaatttacta  12600

tatacattga ccaaaaaagt ttgagatatc tactagatca gcgaattaca actcaaccaa  12660

caatattggg tagccaagtt gctggggtat gagtttgaca ttgtgtataa ggtgggggct  12720

tcaaacaagg ttgttgatgc tctatctaga agagatgaag acaaagaatt gcagggcatt  12780

tctagacctt tctggaaaga cataacaaaa attaatgaag aagttcagaa ggatcccgcg  12840

ttggctaaaa tccgagaaga attgaaggat aatctagatt cacaccctca gtacaccctg  12900

gagtgtgaca tattatactt cagagggagg ttggtcctat tagcttcttc attgtggatt  12960

ccaaagttac tacaagaatt ccagacttct cttatgggag ggcactcggg tatttacata  13020

acttatagaa gaatcactca atcgctttat tggataccaa taaagggaga aatcactaag  13080

tttgtggttg cgtgtcatgt gggccaaaga agtaaatatc aagcatcctc tccagcaggt  13140

ttactacaac ctttgccaat tccaaatgct atttgggaag aaattagtat gaattttatt  13200

gtaggtatgc taaaatcaaa aggg                                          13224
```

<210> SEQ ID NO 7
<211> LENGTH: 6583
<212> TYPE: DNA
<213> ORGANISM: Artificial Sequence
<220> FEATURE:
<223> OTHER INFORMATION: Cassettes

<400> SEQUENCE: 7

```
aattctcagt ccaaagcctc aacaaggtca gggtacagag tctccaaacc attagccaaa     60

agctacagga gatcaatgaa gaatcttcaa tcaaagtaaa ctactgttcc agcacatgca    120

tcatggtcag taagtttcag aaaaagacat ccaccgaaga cttaaagtta gtgggcatct    180

ttgaaagtaa tcttgtcaac atcgagcagc tggcttgtgg ggaccagaca aaaaaggaat    240
```

-continued

```
ggtgcagaat tgttaggcgc acctaccaaa agcatctttg cctttattgc aaagataaag    300
cagattcctc tagtacaagt ggggaacaaa ataacgtgga aaagagctgt cctgacagcc    360
cactcactaa tgcgtatgac gaacgcagtg acgaccacaa aagaattagc ttgagctcag    420
gatttagcag cattccagat tgggttcaat caacaaggta cgagccatat cactttattc    480
aaattggtat cgccaaaacc aagaaggaac tcccatcctc aaaggtttgt aaggaagaat    540
tcgatatcaa gcttgatatc ggaagtttct ctcttgaggg aggttgctcg tggaatggga    600
cacatatggt tgttataata aaccatttcc attgtcatga gattttgagg ttaatatata    660
ctttacttgt tcattatttt atttggtgtt tgaataaatg atataaatgg ctcttgataa    720
tctgcattca ttgagatatc aaatatttac tctagagaag agtgtcatat agattgatgg    780
tccacaatca atgaaatttt tgggagacga acatgtataa ccatttgctt gaataacctt    840
aattaaaagg tgtgattaaa tgatgtttgt aacatgtagt actaaacatt cataaaacac    900
aaccaaccca agaggtattg agtattcacg gctaaacagg ggcataatgg taatttaaag    960
aatgatatta ttttatgtta aaccctaaca ttggtttcgg attcaacgct ataaataaaa   1020
ccactctcgt tgctgattcc atttatcgtt cttattgacc ctagccgcta cacacttttc   1080
tgcgatatct ctgaggtaag cgttaacgta cccttagatc gttctttttc tttttcgtct   1140
gctgatcgtt gctcatatta tttcgatgat tgttggattc gatgctcttt gttgattgat   1200
cgttctgaaa attctgatct gttgtttaga ttttatcgat tgttaatatc aacgtttcac   1260
tgcttctaaa cgataattta ttcatgaaac tattttccca ttctgatcga tcttgttttg   1320
agattttaat ttgttcgatt gattgttggt tggtggatct atatacgagt gaacttgttg   1380
atttgcgtat ttaagatgta tgtcgatttg aattgtgatt gggtaattct ggagtagcat   1440
aacaaatcca gtgttccctt tttctaaggg taattctcgg attgtttgct ttatatctct   1500
tgaaattgcc gatttgattg aatttagctc gcttagctca gatgatagag caccacaatt   1560
tttgtggtag aaatcggttt gactccgata gcggcttttt actatgattg ttttgtgtta   1620
aagatgattt tcataatggt tatatatgtc tactgttttt attgattcaa tatttgattg   1680
ttcttttttt tgcagatttg ttgaccagag atctaccatg gcgcaagtta gcagaatctg   1740
caatggtgtg cagaacccat ctcttatctc caatctctcg aaatccagtc aacgcaaatc   1800
tcccttatcg gtttctctga agacgcagca gcatccacga gcttatccga tttcgtcgtc   1860
gtggggattg aagaagagtg ggatgacgtt aattggctct gagcttcgtc ctcttaaggt   1920
catgtcttct gtttccacgg cgtgcatgct tcacggtgca agcagccgtc cagcaactgc   1980
tcgtaagtcc tctggtcttt ctggaaccgt ccgtattcca ggtgacaagt ctatctccca   2040
caggtccttc atgtttggag gtctcgctag cggtgaaact cgtatcaccg gtcttttgga   2100
aggtgaagat gttatcaaca ctggtaaggc tatgcaagct atgggtgcca gaatccgtaa   2160
ggaaggtgat acttggatca ttgatggtgt tggtaacggt ggactccttg ctcctgaggc   2220
tcctctcgat ttcggtaacg ctgcaactgg ttgccgtttg actatgggtc ttgttggtgt   2280
ttacgatttc gatagcactt tcattggtga cgcttctctc actaagcgtc caatgggtcg   2340
tgtgttgaac ccacttcgcg aaatgggtgt gcaggtgaag tctgaagacg gtgatcgtct   2400
tccagttacc ttgcgtggac caaagactcc aacgccaatc acctacaggg tacctatggc   2460
ttccgctcaa gtgaagtccg ctgttctgct tgctggtctc aacaccccag gtatcaccac   2520
tgttatcgag ccaatcatga ctcgtgacca cactgaaaag atgcttcaag gttttggtgc   2580
```

-continued

```
taaccttacc gttgagactg atgctgacgg tgtgcgtacc atccgtcttg aaggtcgtgg   2640
taagctcacc ggtcaagtga ttgatgttcc aggtgatcca tcctctactg ctttcccatt   2700
ggttgctgcc ttgcttgttc caggttccga cgtcaccatc cttaacgttt tgatgaaccc   2760
aacccgtact ggtctcatct tgactctgca ggaaatgggt gccgacatcg aagtgatcaa   2820
cccacgtctt gctggtggag aagacgtggc tgacttgcgt gttcgttctt ctactttgaa   2880
gggtgttact gttccagaag accgtgctcc ttctatgatc gacgagtatc caattctcgc   2940
tgttgcagct gcattcgctg aaggtgctac cgttatgaac ggtttggaag aactccgtgt   3000
taaggaaagc gaccgtcttt ctgctgtcgc aaacggtctc aagctcaacg gtgttgattg   3060
cgatgaaggt gagacttctc tcgtcgtgcg tggtcgtcct gacggtaagg gtctcggtaa   3120
cgcttctgga gcagctgtcg ctacccacct cgatcaccgt atcgctatga gcttcctcgt   3180
tatgggtctc gtttctgaaa accctgttac tgttgatgat gctactatga tcgctactag   3240
cttcccagag ttcatggatt tgatggctgg tcttggagct aagatcgaac tctccgacac   3300
taaggctgct tgatgagctc aagaattcga gctcggtacc ggatcctaag atcttaggat   3360
cctctagcta gagctttcgt tcgtatcatc ggtttcgaca acgttcgtca agttcaatgc   3420
atcagtttca ttgcgcacac accagaatcc tactgagttt gagtattatg gcattgggaa   3480
aactgttttt cttgtaccat ttgttgtgct tgtaatttac tgtgtttttt attcggtttt   3540
cgctatcgaa ctgtgaaatg gaaatggatg gagaagagtt aatgaatgat atggtccttt   3600
tgttcattct caaattaata ttatttgttt tttctcttat ttgttgtgtg ttgaatttga   3660
aattataaga gatatgcaaa cattttgttt tgagtaaaaa tgtgtcaaat cgtggcctct   3720
aatgaccgaa gttaatatga ggagtaaaac acttgtagtt gtaccattat gcttattcac   3780
taggcaacaa atatatttc agacctagaa aagctgcaaa tgttactgaa tacaagtatg   3840
tcctcttgtg ttttagacat ttatgaactt tcctttatgt aattttccag aatccttgtc   3900
agattctaat cattgcttta taattatagt tatactcatg gatttgtagt tgagtatgaa   3960
aatattttt aatgcattt atgacttgcc aattgattga caacatgcat caatcgacct   4020
gcagccactc gaagcggccc aacccggggg cctatatggc ccggtccggc ggccgcggta   4080
cggtcgactc tagaggatcc ccggcaaaaa catttaatac gtattattta agaaaaaaat   4140
atgtaataat atatttatat tttaatatct attcttatgt attttttaaa aatctattat   4200
atattgatca actaaaatat ttttatatct acacttattt tgcattttta tcaattttct   4260
tgcgtttttt ggcatattta ataatgacta ttctttaata atcaatcatt attcttacat   4320
ggtacatatt gttggaacca tatgaagtgt ccattgcatt tgactatgtg gatagtgttt   4380
tgatccaggc ctccatttgc cgcttattaa ttaatttggt aacagtccgt actaatcagt   4440
tacttatcct tcctccatca taattaatct tggtagtctc gaatgccaca acactgacta   4500
gtctcttgga tcataagaaa aagccaagga acaaaagaag acaaaacaca atgagagtat   4560
cctttgcata gcaatgtcta agttcataaa attcaaacaa aaacgcaatc acacacagtg   4620
gacatcactt atccactagc tgatcaggat cgccgcgtca agaaaaaaaa actggacccc   4680
aaaagccatg cacaacaaca cgtactcaca aaggtgtcaa tcgagcagcc caaaacattc   4740
accaactcaa cccatcatga gcccacacat ttgttgtttc taacccaacc tcaaactcgt   4800
attctcttcc gccacctcat ttttgtttat ttcaacaccc gtcaaactgc atgccacccc   4860
gtggccaaat gtccatgcat gttaacaaga cctatgacta taaatatctg caatctcggc   4920
ccaggttttc atcatcaaga accgggtacc gagctcgagc ctaggggtaa attaaattgt   4980
```

```
gcctgcatct cgggatattt catgtggggt tcatcatatt tgttgaggaa aagaaactcc   5040

cgaaattgaa ttatgcattt atatatcctt tttcatttct agatttcctg aaggcttagg   5100

tgtaggcacc tagctagtag ctacaatatc agcacttctc tctattgata aacaattggc   5160

tgtaatgccg cagtagagga cgatcacaac atttcgtgct ggttactttt tgttttatgg   5220

tcatgatttc aagactagac gttctaccgg agaagcgacc ttagaaattc attatggtgg   5280

caacagctgc tacttcatca tttttccctg ttacttcacc ctcgccggac tctggtggag   5340

caggcagcaa acttggtggt gggcctgcaa accttggagg actaaaatcc aaatctgcgt   5400

cttctggtgg cttgaaggca aaggcgcaag ccccttcgaa aattaatgga accacagttg   5460

ttacatctaa agaaagcttc aagcatgatg atgatctacc ttcgcctccc cccagaactt   5520

ttatcaacca gtcctgcagg tttaaactat cagtgtttga aaatggcttc atgtccggga   5580

aatctacatg gatcagcaaa ggtagatcat catcatgctt gaagctttct ttagatgtaa   5640

caactgtggt tccattaatt ttcgaagggg cttgcgcctt tgccttcaag ccaccagaag   5700

acgcagattt ggattttagt cctccaaggt ttgcaggccc accaccaagt ttgctgcctg   5760

ctccaccaga gtccggcgag ggtgaagtaa cagggaaaaa tgatgaagta gcagctgttg   5820

ccaccataat gaatttctaa ggtcgcttct ccggtagaac gtctagtctt gaaatcatga   5880

ccataaaaca aaaagtaacc agcacgaaat gttgtgatcg tcctctactg cggcattaca   5940

gccaattgtt tatcaataga gagaagtgct gatattgtag ctactagcta ggtgcctaca   6000

cctaagcctt caggaaatct agaaatgaaa aaggatatat aaatgcataa ttcaatttcg   6060

ggagtttctt ttcctcaaca aatatgatga accccacatg aaatatcccg agatgcaggc   6120

acaatttaat ttacccctag gacgcgtaac aaaagagtgc ctcacatttg atgcaatagc   6180

tctgtaatgt ttcattcatt tgcttatttc ggccttgttt ttctcgtatt ctatgggctg   6240

atgtctcata tgggactttt ctactagaga gcctacgtta ctttaccatt atattgtatt   6300

ctttgagaca ttattattat ttttttacct tttgaggaca ctcttttttt gtatttgaag   6360

gaatttattg tttattttgt ttggaatatg tttggttgga tttattcgat tcatatatat   6420

tatataaaag taattatgtt attaagaaac gtagtaagaa cttacaaata taaggatcga   6480

atcccgaact tcatgcaaat caatttacaa cccacacaag tttaacatta aattaacgtg   6540

attggttagt aaattcatgt ttctctgttt aatttgttga att                     6583
```

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8

```
tcccggacat gaagccatt                                                  19
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9

```
tgttatcact gcggtttggc                                                 20
```

-continued

<210> SEQ ID NO 10
<211> LENGTH: 21
<212> TYPE: DNA
<213> ORGANISM: Artificial Sequence
<220> FEATURE:
<223> OTHER INFORMATION: Probe

<400> SEQUENCE: 10
caattgaaga gactcagggt g 21

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
agactcaggg tgttgttatc actgc 25

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cattgctgat ccatgtagat ttcc 24

<210> SEQ ID NO 13
<211> LENGTH: 20
<212> TYPE: DNA
<213> ORGANISM: Artificial Sequence
<220> FEATURE:
<223> OTHER INFORMATION: Probe

<400> SEQUENCE: 13
acatgaagcc atttacaatt 20

<210> SEQ ID NO 14
<211> LENGTH: 20
<212> TYPE: DNA
<213> ORGANISM: Artificial Sequence
<220> FEATURE:
<223> OTHER INFORMATION: Probe

<400> SEQUENCE: 14
atgttgagta tgtcaaatga 20

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
gaaacaaagg atctcaaacc attctt 26

<210> SEQ ID NO 16
<211> LENGTH: 40
<212> TYPE: DNA
<213> ORGANISM: Glycine max

<400> SEQUENCE: 16
aaccattctt tatgttgagt atgtcaaatg aagagactca 40

<210> SEQ ID NO 17
<211> LENGTH: 2370
<212> TYPE: DNA
<213> ORGANISM: Glycine max
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t

<400> SEQUENCE: 17
gggtgttgtt atcactgcgg tttggccttt gggccaaggc actgttgtcc tgaaaaaaat 60
atgagagttg taatactcgc taaggatgag tagattaatg aagacgggga gatcntagga 120
ttaaaaaatg agaatgagga agaatgtgag gaagntttgg agatggtttg ctagcggatg 180
gatttgtcag tttgttccgc aggtgggcta acccagcctc aagcatgaag cttaggtgag 240
aattataggg gcaagaggtg ataatcttga ttgacaatag ggcaagccac aactttatat 300
ccaacaaatt ggtacataaa ttgggactca gcatagatcc cacaaagccc tattatatga 360
gattggggga tagtaaccgc aaatccactc aaggatgttg taagaactta aaaaatagtt 420
gggagcttat accntggtag gatatttcta tctatttaag ttgggaggag tggacctaat 480
tattggagtt gcttagttgg aaacattggg agaaattaag gtgaattgga ggaccctaag 540
tatgtctttt gtccaccaag atcagaatat ggtgatcaag gagatcttgg tttattgaag 600
acaatgatca ttttgagaac attgcaaaaa atagttagca aggaagttga gatgatgttc 660
atgttgtggg taattgaaag caactatgtg gaacaaattg atttaacaaa gaaccaagaa 720
aattagttgt agcaagtact gatagagttt gctacagttt ttcaggacct aagggtttac 780
caccatctag agaggttgat cacaagattg caattaagtc cggggcatat ccagataatg 840
ttaggcctta tcgttacccc cacttacaga agaatgagat aaaaactcta gtggttgaga 900
tgttatgatt ggggattatt agactaagca atagctccta ttctagccca gtaattttgg 960
taaaaaggaa agatggaagt tgacgattat gtatggatta tcaggcttta agtaaggcta 1020
cagtcccaga caagttcctg attcctgtca tgaaagagtt gttggatgag ttaaatggac 1080
ccatccactt ctctaaaata gatctaaagg caaggtatca ccaaatcaga atgcacaaac 1140
ctaccttcag aactcaccaa ggacattatg aatctccagt gatgccattt ggattaacaa 1200
acaccccgac cacgttccaa tgagctatga atgccacact gaaaccgttc cttcgtaggt 1260
atgtggtagt gttctttgat gacattttgg tctatagtaa gtcttgggaa gcccatttgg 1320
atcatttgag ttaggtgttg gccaggttat tagaacatta tttcttcaca aatgttttta 1380
aaaaaaaatg tagttttggt caaattaagg cgggttgctt agggcacgtt atctctaaag 1440
aaggagtttt gatgaggcca ttttgtagtg gccaatgcct aaaactccta agtctttgag 1500
agggtttttg gaacttacag gttattataa aaggtccatt tgcaattatg ggaagatagc 1560
tcgcccattg attgatctat taaagtaagg aaattttaag tggaatgagg atagtattaa 1620
ggcttccata caattacaac aagctattac cacaatacca acactatcca tgcttgattt 1680

-continued

```
ttcaaaacaa ttctccatag aatgtgatgc ctcggggaag ggaattggag ttgttctaac   1740

acaagataga aagcaaattg cttatttcaa caaggcatta aaagatttga ctctttctaa   1800

atctatgtat gaaaaggaat caatggctct tgtcttagcc atacaacatt ggaggcctta   1860

tcttccggat tagaaattta ctatatacat tgaccaaaaa agtttgagat atctactaga   1920

tcagcgaatt acaactcaac caacaatatt gggtagccaa gttgctgggg tatgagtttg   1980

acattgtgta taaggtgggg gcttcaaaca aggttgttga tgctctatct agaagagatg   2040

aagacaaaga attgcagggc atttctagac ctttctggaa agacataaca aaaattaatg   2100

aagaagttca gaaggatccc gcgttggcta aaatccgaga agaattgaag gataatctag   2160

attcacaccc tcagtacacc ctggagtgtg acatattata cttcagaggg aggttggtcc   2220

tattagcttc ttcattgtgg attccaaagt tactacaaga attccagact tctcttatgg   2280

gagggcactc gggtatttac ataacttata gaagaatcac tcaatcgctt tattggatac   2340

caataaaggg agaaatcact aagtttgtgg                                     2370


<210> SEQ ID NO 18
<211> LENGTH: 106
<212> TYPE: DNA
<213> ORGANISM: Artificial Sequence
<220> FEATURE:
<223> OTHER INFORMATION: RB/RB junction

<400> SEQUENCE: 18

cagaactttt atcaaccagt cctgcaggtt taaactatca gtgtttgaaa atggcttcat     60

gtccgggaaa tctacatgga tcagcaaagg tagatcatca tcatgc                   106


<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19

ctgaccttgt tgaggctttg gactgag                                         27


<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20

ggaacagtag tttactttga ttgaagattc                                      30
```

SOYBEAN TRANSGENIC EVENT MON87705 AND METHODS FOR DETECTION THEREOF

CROSS-REFERENCE TO RELATED APPLICATIONS

This application is a divisional of U.S. application Ser. No. 13/930,925, filed Jun. 28, 2013 (allowed), which is a divisional of U.S. application Ser. No. 13/670,136, filed Nov. 6, 2012, now U.S. Pat. No. 8,692,080, issued Apr. 8, 2014, which is a divisional of U.S. application Ser. No. 12/568,321, filed Sep. 28, 2009, now U.S. Pat. No. 8,329,989, issued Dec. 11, 2012, The present application which claims the benefit of U.S. Provisional Application Ser. No. 61/100,859, filed on Sep. 29, 2008, all of which are incorporated herein by reference in their entireties.

INCORPORATION OF SEQUENCE LISTING

This application contains an electronic equivalent paper copy of the sequence listing submitted herewith electronically via EFS web and a computer-readable form of the sequence listing submitted herewith electronically via EFS web which contains a file named "seqlist.txt", which is 51,100 bytes in size (measured in WINDOWS) and which was created on Jan. 11, 2017. The sequence listings submitted herewith as electronic equivalents of a paper copy and computer-readable form are herein incorporated by reference.

FIELD OF THE INVENTION

The present invention relates to transgenic soybean event MON87705 and plant parts and seed thereof. The event exhibits an oil composition comprising altered fatty acid levels. The invention also relates to methods for detecting the presence of soybean event in a biological sample, and provides nucleotide sequences that are capable of doing so.

BACKGROUND OF THE INVENTION

Soybean is an important crop and is a primary food source in many areas of the world. The methods of biotechnology have been applied to soybean for improvement of agronomic traits and the quality of the product. One such quality trait is a soybean oil comprising altered fatty acid levels.

It would be advantageous to be able to detect the presence of transgene/genomic DNA of a particular plant in order to determine whether progeny of a sexual cross contain the transgene/genomic DNA of interest. In addition, a method for detecting a particular plant would be helpful when complying with regulations requiring the pre-market approval and labeling of foods derived from the recombinant crop plants.

Soybean oils have been modified by various breeding methods to create benefits for specific markets. However, a soybean oil that is broadly beneficial to major soybean oil users such as consumers of salad oil, cooking oil and frying oil, and industrial markets such as biodiesel and biolube markets, is not available. Prior soybean oils were either too expensive or lacked an important food quality property such as oxidative stability, good fried food flavor or saturated fat content or an important biodiesel property such as appropriate nitric oxide emissions or cold tolerance or cold flow.

Soybean oil typically contains approximately 20% oleic acid. Oleic acid has one double bond, but is still relatively stable at high temperatures, and oils with high levels of oleic acid are suitable for cooking and other processes where heating is required. Recently, increased consumption of high oleic oils has been recommended, because oleic acid appears to lower blood levels of low density lipoproteins ("LDLs") without affecting levels of high density lipoproteins ("HDLs"). However, some limitation of oleic acid levels is desirable, because when oleic acid is degraded at high temperatures, it creates negative flavor compounds and diminishes the positive flavors created by the oxidation of linoleic acid. Neff et al., JAOCS, 77:1303-1313 (2000); Warner et al., J. Agric. Food Chem. 49:899-905 (2001). It is thus preferable to use oils with oleic acid levels that are 65-85% or less by weight, in order to limit off-flavors in food applications such as frying oil and fried food. Other preferred oils have oleic acid levels that are greater than 55% by weight in order to improve oxidative stability.

For many oil applications, saturated fatty acid levels of less than 8% by weight or even less than about 2-3% by weight are desirable. Soybean oil typically contains about 16-20% saturated fatty acids: 13-16% palmitate and 3-4% stearate (see generally Gunstone et al., The Lipid Handbook, Chapman & Hall, London (1994)). Saturated fatty acids have high melting points which are undesirable in many applications. When used as a feedstock or fuel, saturated fatty acids cause clouding at low temperatures and confer poor cold flow properties such as pour points and cold filter plugging points to the fuel. Oil products containing low saturated fatty acid levels may be preferred by consumers and the food industry because they are perceived as healthier and/or may be labeled as "saturated fat free" in accordance with FDA guidelines. In addition, low saturate oils reduce or eliminate the need to winterize the oil for food applications such as salad oils. In biodiesel and lubricant applications oils with low saturated fatty acid levels confer improved cold flow properties and do not cloud at low temperatures.

Soybean lines that produce seed with mid-oleic and low saturate content would be desirable. Methods disclosed here enable production of soybean seeds that have oleic acid levels in the mid oleic range of 55-80% and saturated fatty acid levels of less than 8%.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., 1988 Ann. Rev. Genet 22:421-477). For this reason, it is often necessary to screen a large number of events in order to identify an event characterized by optimal expression of an introduced gene of interest. For example, it has been observed in plants and in other organisms that there may be wide variation in the levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce several hundred to several thousand different events and screen the events for a single event that has the desired transgene expression levels and patterns for commercial purposes. An event that has the desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are suitably adapted to specific local growing conditions.

It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for canola event GT73 is demonstrated. In this study, event-specific primers and probes were designed based upon the sequences of the genome/transgene junctions for each event. Transgenic plant event-specific DNA detection methods have also been described in U.S. Pat. Nos. 6,893,826; 6,825,400; 6,740,488; 6,733,974; 6,689,880; 6,900,014 and 6,818,807.

This invention relates to the transgenic soybean (*Glycine max*) plant MON87705 with an oil composition comprising altered fatty acid levels and to the DNA construct of soybean plant MON87705 and the detection of the transgene/genomic insertion region in soybean MON87705 and progeny thereof.

SUMMARY OF THE INVENTION

The present invention includes a transgenic soybean plant designated MON87705 and progeny that are indistinguishable from soybean event MON87705 (to the extent that such progeny also contain at least one allele that corresponds to the inserted transgenic DNA) thereof having seed deposited with American Type Culture Collection (ATCC) with Accession No. PTA-9241. Another aspect of the invention is the progeny plants, or seeds, or regenerable parts of the plants and seeds of the soybean event MON87705. The invention also includes plant parts of the soybean event MON87705 that include, but are not limited to pollen, ovule, flowers, shoots, roots, stems, leaves, pods, seeds and meristematic tissues. Novel genetic compositions contained in the genome of MON87705 and products from MON87705 such as oil, meal, flour, food products, protein supplements and biomasses remaining in a field from which soybean plants corresponding to MON87705 have been harvested are aspects of this invention.

The invention provides a soybean plant capable of producing a seed having an oil composition comprising approximately 55-80% oleic acid by weight and less than 8% saturated fatty acid by weight, wherein genetic determinants for said oil composition is obtainable from soybean having ATCC Accession No. PTA-9241.

According to one aspect of the invention, compositions and methods are provided for detecting the presence of the transgene/genomic insertion region from a novel soybean plant designated MON87705. DNA sequences are provided that comprise at least one junction sequence of MON87705 selected from the group consisting of SEQ ID NO: 1 ([A] corresponding to positions 3449 through 3468 of SEQ ID NO: 6 [F], FIG. 2), SEQ ID NO: 2 ([B] corresponding to positions 10700 through 10719 of SEQ ID NO: 6 [F], FIG. 2) and SEQ ID NO: 18 (corresponding to positions 9266 through 9371 of SEQ ID NO: 6 [F], FIG. 2) and complements thereof; wherein a junction sequence is a nucleotide sequence that spans the point at which heterologous DNA inserted into the genome is linked to the soybean cell genomic DNA and detection of this sequence in a biological sample containing soybean DNA is diagnostic for the presence of the soy event MON87705 DNA in said sample (FIG. 2). Such junction sequences can contain at least one of the sequences listed under SEQ ID NO: 1, 2, 18 and the complements thereof. A soybean plant, soybean seed from the plant and progeny of the plant comprising these DNA molecules is an aspect of this invention.

DNA sequences that comprise novel transgene/genomic insertion region, SEQ ID NO: 3 [C], SEQ ID NO: 4 [D] and SEQ ID NO: 5 [E] or SEQ ID NO: 1 [A] and SEQ ID NO: 2 [B] (see FIG. 2) from soybean event MON87705 are aspects of this invention. The soybean plant, seed and progeny comprising these molecules are also aspects of this invention.

According to another aspect of the invention, two DNA molecules are provided for use in a DNA detection method, where the first DNA molecule comprises at least 11 or more, at least 12 or more, or at least 13 or more contiguous polynucleotides of any portion of the transgene region of the DNA molecule of SEQ ID NO: 5 and a DNA molecule of similar length of any portion of a 5' flanking soybean genomic DNA region of SEQ ID NO: 3, where these DNA molecules when used together are useful as DNA primers in a DNA amplification method that produces an amplicon. The amplicon produced using these DNA primers in the DNA amplification method is diagnostic for soybean event MON87705 when the amplicon contains SEQ ID NO: 1. Any amplicon produced by DNA primers homologous or complementary to any portion of SEQ ID NO: 3 and SEQ ID NO: 5, and any amplicon that comprises SEQ ID NO: 1 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 5 and a DNA molecule of similar length of any portion of a 3' flanking soybean genomic DNA of SEQ ID NO: 4, where these DNA molecules are useful as DNA primers in a DNA amplification method. The amplicon produced using these DNA primers in the DNA amplification method is diagnostic for soybean event MON87705 when the amplicon contains SEQ ID NO: 2. Any amplicons produced by DNA primers homologous or complementary to any portion of SEQ ID NO: 4 and SEQ ID NO: 5, and any amplicon that comprises SEQ ID NO: 2 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 5 or their complements wherein one primer is derived from sequence 5' to SEQ ID NO: 18 and the other primer is derived from sequence 3' to SEQ ID NO: 18 where these DNA molecules are useful as DNA primers in a DNA amplification method. The amplicon produced using these DNA primers in the DNA amplification method is diagnostic for soybean event MON87705 when the amplicon contains SEQ ID NO: 18. Any amplicons produced by DNA primers homologous or complementary to any portion of SEQ ID NO: 5 and any amplicon that comprises SEQ ID NO: 18 is an aspect of the invention.

According to another aspect of the invention, methods of detecting the presence of DNA corresponding to the soybean event MON87705 in a sample are provided. Such methods comprise: (a) contacting the sample comprising DNA with a primer set that, when used in a nucleic acid amplification reaction with genomic DNA from soybean event MON87705, produces an amplicon that is diagnostic for soybean event MON87705; (b) performing a nucleic acid amplification reaction, thereby producing the amplicon; and (c) detecting the amplicon wherein said amplicon comprises one or more or the sequences listed under SEQ ID NOs: 1, 2 and 18.

Another aspect of the invention is a soybean plant, or seed, or product containing the event of the plant or seed of MON87705 wherein the genomic DNA comprises a DNA molecule consisting essentially of the nucleotide sequence of SEQ ID NO: 3 from about positions 1 to 3458, the nucleotide sequence of SEQ ID NO: 5 from about positions 1 to 7251 and the nucleotide sequence of SEQ ID NO: 4 from about positions 1 to 2515 (the contig of which is presented as SEQ ID NO: 6), and complements thereof. A further aspect of the invention is a soybean plant, or seed, or product derived from the plant or seed of MON87705 wherein the genomic DNA comprises a DNA molecule consisting essentially of the nucleotide sequence of SEQ ID NO: 6 from about positions 1 to 13224 and complements thereof. A soybean plant, or seed, or product derived from the plant or seed MON87705, in which the genomic DNA when isolated from the soybean plant, or seed, or product comprises a DNA molecule incorporating SEQ ID NOs: 1, 2 or 18, and complements thereof. In one aspect of the invention, the DNA molecule contains the soybean event MON87705. In another aspect, two copies of the DNA molecule containing the soybean event MON87705 are present in the soybean plant. In another aspect, one copy of the DNA molecule containing the soybean event MON87705 is present in the soybean plant.

Another aspect of the invention is a soybean plant, or seed, or product containing the event of the plant or seed of MON87705, in which the genomic DNA when isolated from the soybean plant, or seed, or product produces an amplicon in a DNA amplification method, where said amplicon comprises at least one sequence from the group consisting of SEQ ID NOs: 1, 2 and 18.

In another aspect, seeds of the soybean plants may be placed in a container. As used herein, a container is any object capable of holding such seeds. A container preferably contains greater than about 500, 1,000, 5,000, or 25,000 seeds where at least about 10%, 25%, 50%, 75% or 100% of the seeds are derived from a plant of the present invention. The present invention also provides a container of over about 10,000, more preferably about 20,000, and even more preferably about 40,000 seeds where over about 10%, more preferably about 25%, more preferably 50% and even more preferably about 75% or 90% of the seeds are seeds derived from a plant of the present invention. The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

Another aspect of the invention provides a method for detecting the presence or absence of soybean transgenic event MON87705 in a biological sample comprising a) extracting DNA from said sample; and b) assaying the presence or absence of a polynucleotide having a sequence corresponding to that shown under SEQ ID NOs: 1, 2 or 18, whereby the presence or absence of soybean event MON87705 in said sample can be ascertained.

According to another aspect of the invention, methods of detecting the presence of DNA corresponding to the MON87705 event in a sample, comprising: (a) contacting the sample with a probe that hybridizes under stringent hybridization conditions with a sequence selected from the group consisting of SEQ ID NO: 1 and SEQ ID NO: 2, and their complements, and does not hybridize under the stringent hybridization conditions with soybean plant DNA that does not comprise SEQ ID NO: 1 and SEQ ID NO: 2; (b) subjecting the sample and probe to stringent hybridization conditions; and (c) detecting binding of the probe to said sample; wherein binding is diagnostic for the presence of said DNA in said sample. Another aspect of the invention is a probe comprising from about 11- to about 20 consecutive nucleotides in length for use in detecting the presence of soybean event MON87705 in a biological sample, wherein said consecutive nucleotides are selected from the group consisting of SEQ ID NO: 1 and SEQ ID NO: 2, and their complements. The probe may be a deoxyribonucleic acid, a ribonucleic acid or a nucleotide analogue. The probe may be labeled with at least one fluorophore.

Another aspect of the invention is a method of determining zygosity of the progeny of soybean event MON87705, the method comprising (a) contacting the sample comprising soybean DNA with the primer set SQ21928 (SEQ ID NO: 11), SQ20901 (SEQ ID NO: 12), and the probe 6FAM™-labeled PB10164 (SEQ ID NO: 13) and that when used in a nucleic-acid amplification reaction with genomic DNA from soybean event MON87705, produces a first amplicon, releasing a fluorescent signal from the combination of primers SQ21928 and SQ20901 and a 6FAM™-labeled primer/probe, PB10164 that is diagnostic for soybean event MON87705 (b) performing a nucleic acid amplification reaction, thereby producing the first amplicon; and (c) detecting said first amplicon; and (d) contacting the sample comprising soybean DNA with the primer set, SQ21928 (SEQ ID NO: 11) and SQ21905 (SEQ ID NO: 15), and a VIC™-labeled PB10335 (SEQ ID NO: 14) that when used in a nucleic-acid amplification reaction with genomic DNA from soybean plants produces a second amplicon, releasing a fluorescent signal that is diagnostic of the wild-type soybean genomic DNA homologous to the soybean genomic region of a transgene insertion identified as soybean event MON87705; (e) performing a nucleic acid amplification reaction, thereby producing the second amplicon and (f) detecting said second amplicon; and (g) comparing the first and second amplicons in a sample, wherein the presence of both amplicons indicates the sample is heterozygous for the transgene insertion.

Another aspect of the invention is a method of determining zygosity of the progeny of soybean event MON87705, the method comprising (a) contacting the sample comprising soybean DNA with the primer set SQ21928 (SEQ ID NO: 11), SQ20901 (SEQ ID NO: 12), and SQ21905 (SEQ ID NO: 15), that when used in a nucleic-acid amplification reaction with genomic DNA from soybean event MON87705, produces a first amplicon from the combination of primers SQ21928 and SQ20901 that is diagnostic for soybean event MON87705 (b) performing a nucleic acid amplification reaction, thereby producing the first amplicon; and (c) detecting said first amplicon; and (d) contacting the sample comprising soybean DNA with the primer set, SQ21928 and SQ21905, that when used in a nucleic-acid amplification reaction with genomic DNA from soybean plants produces a second amplicon from the combination of primers SQ21928 and SQ21905 that is diagnostic of the wild-type soybean genomic DNA homologous to the soybean genomic region of a transgene insertion identified as soybean event MON87705; (e) performing a nucleic acid amplification reaction, thereby producing the second amplicon and (0 detecting said second amplicon; and (g) comparing the first and second amplicons in a sample, wherein the presence of both amplicons indicates the sample is heterozygous for the transgene insertion.

The invention also provides a composition having a DNA molecule selected from the group consisting of SEQ ID NOs: 1, 2 and 18, wherein said composition is a commodity product selected from the group consisting of soybean meal, soy flour, soy protein concentrate, soy protein isolates, texturized soy protein concentrate, hydrolyzed soy protein and whipped topping.

Another aspect of the invention is a method for detecting the presence of a nucleotide sequence diagnostic for the presence of soybean event MON87705 in a biological sample, comprising detecting the presence of a nucleotide sequence wherein said sequence is selected from the group consisting of SEQ ID NOs: 1, 2 and 18, wherein said biological sample is selected from the group consisting of soybean meal, soy flour, soy protein concentrate, soy protein isolates, texturized soy protein concentrate, hydrolyzed soy protein and whipped topping.

Kits for the detection of soybean event MON87705 in a soybean sample are provided that comprise nucleotide components designed based on detecting one or more sequences shown under SEQ ID NOs: 1, 2 and 18. Kits for the detection of soybean event MON87705 are provided which use primers designed from SEQ ID NO: 3, 4 or 5. An amplicon produced using said kit is diagnostic for MON87705 when the amplicon contains one or more nucleotide sequences listed under SEQ ID NOs: 1, 2 and 18.

Another aspect of the invention is a method for producing a soybean plant comprising altered fatty acid levels, comprising crossing a plant comprising soybean event MON87705 with a soybean plant lacking soybean event MON87705 to obtain a plant comprising said soybean event MON87705 and altered fatty acid levels, wherein a representative sample of seed comprising said event was deposited under ATCC Accession No. PTA-9241.

Also provided is a method of producing a soybean variety comprising soybean event MON87705, comprising backcrossing soybean event MON87769 into said variety, wherein a representative sample of seed comprising said event was deposited under ATCC Accession No. PTA-9241.

Another aspect of the invention is a soybean plant capable of producing seeds having an oil composition comprising approx. 55-80% oleic acid and less than 8% saturated fatty acid, wherein genetic determinants for said oil composition is obtainable from soybean having ATCC Accession No. PTA-9241. Also provided is an oil composition obtained from seeds of the soybean plant and a commodity product derived from the oil selected from the group consisting of cooking oil, salad oil, shortening, lecithin, nontoxic plastics, printing inks, lubricants, waxes, hydraulic fluids, electric transformer fluids, solvents, cosmetics, hair care products and biodiesel.

An oil of the present invention may be blended with other oils. In one aspect, the oil produced from plants of the present invention or generated by a method of the present invention constitutes greater than 0.5%, 1%, 5%, 10%, 25%, 50%, 75% or 90% by volume or weight of the oil component of any product. In another aspect, the oil preparation may be blended and can constitute greater than 10%, 25%, 35%, 50% or 75% of the blend by volume. Oil produced from a plant of the present invention can be admixed with one or more organic solvents or petroleum distillates.

A further aspect of the invention is a genome of a soybean cell comprising a polynucleotide having a sequence selected from the group consisting of sequences listed under SEQ ID NO: 1, 2 and 18.

Another aspect of the invention is a soybean plant, or seed, or seed progeny, or product derived from the plant or seed of MON87705. Seed for sale for planting or for making commodity products is an aspect of the invention. Such commodity products include, but are not limited to, whole or processed soy seeds, animal feed, vegetable oil, meal, flour, nontoxic plastics, printing inks, lubricants, waxes, hydraulic fluids, electric transformer fluids, solvents, cosmetics, hair care products, soymilk, soy nut butter, natto, tempeh, soy protein concentrate, soy protein isolates, texturized soy protein concentrate, hydrolyzed soy protein, whipped topping, cooking oil, salad oil, shortening, lecithin, edible whole soybeans (raw, roasted, or as edamamé), soymilk, soy yogurt, soy cheese, tofu, yuba and biodiesel.

The foregoing and other aspects of the invention will become more apparent from the following detailed description.

BRIEF DESCRIPTION OF THE SEQUENCES

Figure 1:
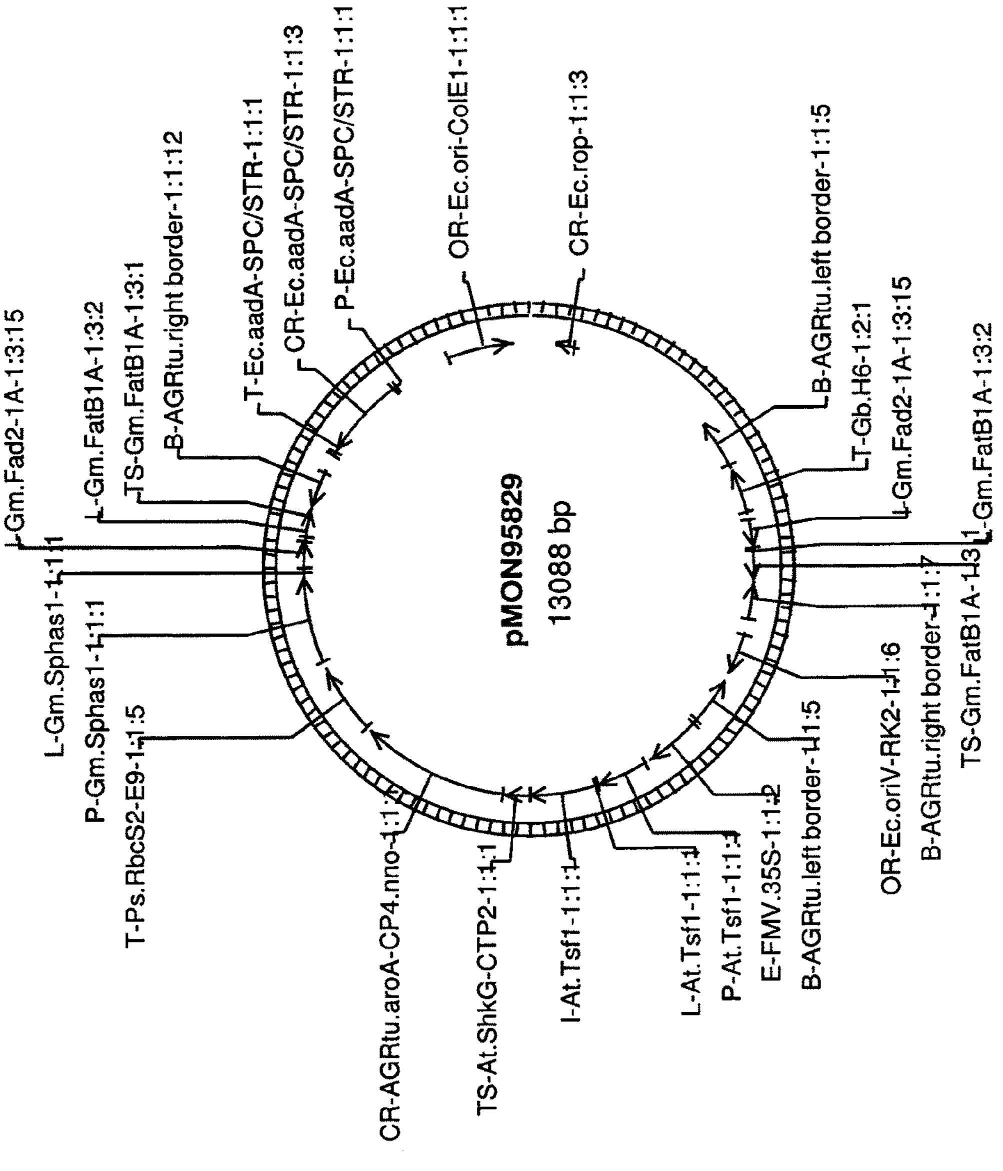
FIG. 1. Map of binary transformation vector, pMON95829 that was used to generate soybean plant MON87705.

SEQ ID NO: 1—A 20 nucleotide sequence representing the 5' left border junction between the soybean genomic DNA and the integrated T-DNA. This sequence corresponds to positions 3413 to 3432 of SEQ ID NO: 6. In addition, SEQ ID NO: 1 ([A] of FIG. 2) is a nucleotide sequence corresponding to positions 3432 through 3422 of SEQ ID NO: 3 ([C], see FIG. 2) and the integrated 5' left border of the integrated T-DNA corresponding to positions 1 through 10 of SEQ ID NO: 5 ([E], see FIG. 2).

SEQ ID NO: 2—A 20 nucleotide sequence representing the 3' left border junction between the integrated T-DNA and the soybean genomic DNA. This sequence corresponds to positions 10664 to 10683 of SEQ ID NO: 6. In addition, SEQ ID NO: 2 ([B], see FIG. 2) is a nucleotide sequence corresponding positions 7242 through 7251 of SEQ ID NO: 5 ([E], see FIG. 2) and the 3' flanking sequence corresponding to positions 1 through 10 of SEQ ID NO: 4 ([D], see FIG. 2).

SEQ ID NO: 3—The 5' sequence flanking the inserted DNA of MON87705 up to the T-DNA insertion.

SEQ ID NO: 4—The 3' sequence flanking the inserted DNA of MON87705 up to the T-DNA insertion.

SEQ ID NO: 5—The sequence of the inserted T-DNAs, including residual border sequence after integration.

SEQ ID NO: 6—A 13188 bp nucleotide sequence representing the contig of the 5' sequence flanking the inserted DNA of MON87705 (SEQ ID NO: 3), the sequence of the integrated expression cassette (SEQ ID NO: 5) and the 3' sequence flanking the inserted DNA of MON87705 (SEQ ID NO: 4).

SEQ ID NO: 7—A 6583 bp nucleotide sequence representing the aroA-CP4 expression cassette and the FAD2-1A/FATB suppression cassette as assembled in MON87705 from the co-integration of the pMON95829 T-DNAs.

SEQ ID NO: 8—Primer SQ20129 used to identify the MON87705 event. Primer SQ20129 corresponds to a region in the 3' of the inserted T-DNA close to the 3' left border corresponding to positions 10645 to 10663 of SEQ ID NO: 6. A PCR amplicon produced using the combination of primers SQ20129 and SQ20130 is positive for the presence of the event MON87705.

SEQ ID NO: 9—Primer SQ20130 used to identify the MON87705. Primer SQ20130 is complimentary to the region 3' of the T-DNA insertion border corresponding to positions 10688 to 10707 of SEQ ID NO: 6. A PCR amplicon produced using the combination of primers SQ20129 and SQ20130 is positive for the presence of the event MON87705.

SEQ ID NO: 10—Probe PB10043 used to identify the MON87705 event. This probe is a 6FAM™-labeled synthetic oligonucleotide whose sequence corresponds to positions 10666 to 10686 of SEQ ID NO: 6. Release of a fluorescent signal in an amplification reaction using primers SQ20129 and SQ20130 in combination with 6FAM™-labeled probe PB10043 is diagnostic of event MON87705.

SEQ ID NO: 11—Primer SQ21928 used to identify the MON87705 event. Primer SQ21928 is complimentary to the region 3' of the T-DNA insertion border corresponding to positions 10675 to 10699 of SEQ ID NO: 6. A PCR amplicon produced using the combination of primers SQ20901 and SQ21928 is positive for the presence of the event MON87705. Primer SQ21928 is also used to determine zygosity of MON87705 events. Detection of a PCR amplicon and the release of fluorescent signal using 6FAM™-labeled Probe PB10335 and primers SQ21928 and SQ21905 is positive for presence of wild type in a zygosity assay. Eighteen base pairs of the sequence corresponds to positions 1053 to 1070 of SEQ ID NO: 6 with the remaining seven base pairs corresponding to seven base pairs in the forty base pair region of wild type sequence shown as SEQ ID NO: 17 which was lost in the generation of the MON87705 event.

SEQ ID NO: 12—Primer SQ20901 used to identify the MON87705 event. Primer SQ20901 corresponds to a region in the 3' of the inserted T-DNA close to the 3' left border corresponding to positions 10624 to 10647 of SEQ ID NO: 6. A PCR amplicon produced from the combination of primers SQ21928 and SQ20901 is positive for the presence of the event MON87705.

SEQ ID NO: 13—Probe PB10164 used to identify the MON87705 event. This probe is a 6FAM™-labeled synthetic oligonucleotide whose sequence corresponds to positions 10651 to 10670 of SEQ ID NO: 6. Release of a fluorescent signal in an amplification reaction using primers SQ21928 and SQ20901 in combination with 6FAM™-labeled probe PB10164 is diagnostic of event MON87705.

SEQ ID NO: 14—Probe PB10335 used to determine zygosity of MON87705 events. This probe is a VIC™-labeled synthetic oligonucloetide whose sequence corresponds to a region of the wild-type genomic DNA. A PCR amplicon produced using primers SQ21928 and SQ21905 causes the release of a fluorescent signal using probe PB10335 which is positive for the presence of the wild-type allele in a zygosity assay for event MON87705. This sequence corresponds to positions 12 to 31 of the forty base pair wild type sequence listed as SEQ ID NO: 17 which was lost in the generation of the MON87705 event.

SEQ ID NO: 15—Primer SQ21905 used to determine zygosity of MON87705 events. Detection of a PCR amplicon using 6FAM™-labeled Probe PB10335 and primers SQ21928 and SQ21905 is positive for presence of wild type in a zygosity assay. Sixteen base pairs of sequence corresponds to positions 1037 to 1052 of SEQ ID NO: 6 while this primer continues ten base pairs into the forty base pair region of wild type sequence listed as SEQ ID NO: 16 which was lost in the generation of the MON87705 event.

SEQ ID NO: 16—Forty base pair sequence that was lost at the junction of the tandem repeat sequence (SEQ ID NO: 17) and the 5' genomic sequences. This sequence is found in the wild type and would have been located between base pair 1052 and 1053 in SEQ ID NO: 6 had it not been lost during the generation of the MON87705 event. Due to the duplication of the genomic sequence upon the generation of the MON87705 event, the terminal twelve bases of sequence is also located at position 10670 to 10681 of SEQ ID NO: 6, but the remaining twenty eight base pairs are completely absent from the MON87705 event and therefore may be utilized to identify the wild type in an assay for zygosity.

SEQ ID NO: 17—This 2370 bp sequence is the portion of the wild type genomic sequences which was apparently duplicated upon generation of the MON87705 event. This region of duplication corresponds to position 1053 to 3422 and is nearly identical to position 10682 to 13051 of SEQ ID NO: 6. Duplicate Genomewalker™ based clones of this region shared two mismatches in the repeat located on the 5' end of the insert when compared to the 3' end and the soy genomic sequence. The two altered bases in the 5' repeat, along with the deletion found on the 5' end of the duplication (SEQ ID NO:16) leads us to the additional that the tandem sequences corresponding to position 1053 to 3422 is the newly generated sequence while the sequence corresponding to position 10682 to 13051 is the original wild type sequence.

SEQ ID NO: 18—This 106 bp sequence spans the right border to right border junction generated upon the co-integration of the two pMON95829 T-DNAs to yield event MON87705. It starts and ends with twenty bases of the suppression target FATB, one from each arm of the inverted repeat, and contains residual border sequences and inserted sequences generated in the integration of the sequences found in the MON87705 event. This sequence corresponds to position 9230 to 9335 of SEQ ID NO: 6. Although this sequence lies within the suppression cassette, due to the random nature of the assembly of the two T-DNAs in vivo, the sequence combination is unique to the MON87705 event.

SEQ ID NO: 19—Primer 24894 used in the secondary (nested) PCR in combination with AP2 for amplification of the Genomewalker™-derived 5' flank extension. This sequence corresponds to position 3722 to 3748 of SEQ ID NO: 6.

SEQ ID NO: 20—Primer 24895 used in the primary PCR in combination with AP1 for amplification of the Genomewalker™-derived 5' flank extension. This sequence corresponds to position 3798 to 3827 of SEQ ID NO: 6.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular,* 5th edition, Springer-Verlag: New York, 1991; and Lewin, Genes V, Oxford University Press: New York, 1994.

As used herein, the term "soybean" means *Glycine max* and includes all plant varieties that can be bred with soybean, including wild soybean species as well as those plants belonging to *Glycine soja* that permit breeding between species.

"Glyphosate" refers to N-phosphonomethylglycine and its salts. N-phosphonomethylglycine is a well-known herbicide that has activity on a broad spectrum of plant species.

"Desaturase" refers to a polypeptide that can desaturate or catalyze formation of a double bond between consecutive carbons of one or more fatty acids to produce a mono- or poly-unsaturated fatty acid or a precursor thereof. Of particular interest are polypeptides that can catalyze the conversion of oleic acid to linoleic acid or linoleic acid to α-linolenic acid, which includes enzymes which desaturate at the 12 or 15 positions. Considerations for choosing a specific polypeptide having desaturase activity include, but are not limited to, the pH optimum of the polypeptide, whether the polypeptide is a rate limiting enzyme or a component thereof, whether the desaturase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s). An endogenous desaturase may also be the target of gene suppression.

"Thioesterase" refers to a polypeptide that can hydrolyze the thioester bond of molecules (splitting of an ester bond into acid and alcohol, in the presence of water) specifically at a thiol group. Of particular interest are polypeptides that can catalyze the hydrolysis of the thioester bond contained in acyl-acyl-carrier proteins (acyl-ACP), especially stearoyl- and palmitoyl-ACP substrates. Such hydrolysis produces a free fatty acid and ACP, thereby terminating the fatty acid biosynthesis of plants located in the plastid and readies the fatty acid for export to the cytoplasm. Considerations for choosing a specific polypeptide having thioesterase activity include, but are not limited to, the pH optimum of the polypeptide, whether the polypeptide is a rate limiting enzyme or a component thereof and whether the thioesterase used is essential for increased production of saturated fatty acids. The expressed polypeptide preferably has characteristics that are compatible with the biochemical environment of its location in the host cell. For example, the polypeptide may have to compete for substrate(s). An endogenous thioesterase may also be the target of gene suppression.

A "commodity product" refers to any product which is comprised of material derived from soybean or soybean oil and is sold to consumers. Processed soybeans are the largest source of protein feed and vegetable oil in the world. The soybean plant MON87705 can be used to manufacture commodities typically acquired from soy. Soybeans of MON87705 can be processed into meal, flour, or oil as well as be used as a protein or oil source in animal feeds for both terrestrial and aquatic animals. Soybeans and soybean oils from MON87705 can be used in the manufacture of many different products, not limited to, nontoxic plastics, printing inks, lubricants, waxes, hydraulic fluids, electric transformer fluids, solvents, cosmetics, and hair care products. Soybeans and oils of MON87705 can be suitable for use in a variety of soyfoods made from whole soybeans, such as soymilk, soy nut butter, natto, and tempeh, and soyfoods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin. Whole soybeans are also edible, and are typically sold to consumers raw, roasted, or as edamamé. Soymilk, which is typically produced by soaking and grinding whole soybeans, may be consumed without other processing, spray-dried, or processed to form soy yogurt, soy cheese, tofu, or yuba.

Oils of MON87705 can be used to make biodiesel. The use of biodiesel in conventional diesel engines results in substantial reductions of pollutants such as sulfates, carbon monoxide, and particulates compared to petroleum diesel fuel, and use in school buses can greatly reduce exposure to toxic diesel exhaust. Biodiesel is typically obtained by extracting, filtering and refining soybean oil to remove free fats and phospholipids, and then transesterifying the oil with methanol to form methyl esters of the fatty acids (see for example U.S. Pat. No. 5,891,203). The resultant soy methyl esters are commonly referred to as "biodiesel." The oil derived from MON87705 may also be used as a diesel fuel without the formation of methyl esters, such as, for example, by mixing acetals with the oil (see for example U.S. Pat. No. 6,013,114). The seeds of MON87705 used to make said oils can be identified by the methods of the present invention. It is expected that purified oil from MON87705 event seeds or mixtures of seeds some or all of which are MON87705 will have relatively no DNA available for testing. However, the seeds from which the oils are extracted can be characterized with the method of the present invention to identify the presence of the MON87705 event within the population of seeds used to make said oils. Also, plant waste from the process used to make said oils can be used in the methods of the present invention to identify the presence of MON87705 events within a mixture of seeds processed to make said oils. Likewise, plant debris left after making a commodity product, or left behind following harvest of the soybean seed, can be characterized by the methods of the present invention to identify MON87705 events within the raw materials used to make said commodity products.

The present invention also includes a blended or non-blended soybean oil of MON87705. Such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety, wherein the progeny comprises the heterologous DNA. Even after repeated back-crossing to a recurrent parent, the inserted DNA and flanking DNA from the original transformation may be present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. The present invention relates to the event MON87705 DNA, plant cells, tissues, seeds and processed products derived from MON87705.

It is also to be understood that two different transgenic plants, or a transgenic plant and a wild-type plant, can also be mated to produce offspring that contain two independently segregating added, exogenous genes. The offspring can be homozygous or heterozygous for the genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

As used herein when referring to an "isolated DNA molecule", it is intended that the DNA molecule be one that is present, alone or in combination with other compositions, but not within its natural environment. For example, a coding sequence, intron sequence, untranslated leader sequence, promoter sequence, transcriptional termination sequence, and the like, that are naturally found within the DNA of a soybean genome are not considered to be isolated from the soybean genome so long as they are within the soybean genome. However, each of these components, and subparts of these components, would be "isolated" within the scope of this disclosure so long as the structures and components are not within the soybean genome. For the purposes of this disclosure, any transgenic nucleotide sequence, i.e., the nucleotide sequence of the DNA inserted into the genome of the cells of the soybean plant event MON87705 would be considered to be an isolated nucleotide sequence whether it is present within the plasmid used to transform soybean cells from which the MON87705 event arose, within the genome of the event MON87705, present in detectable amounts in tissues, progeny, biological samples or commodity products derived from the event MON87705. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the event MON87705. For that matter, the junction sequences as set forth at SEQ ID NOs: 1, 2 and 18, and nucleotide sequences derived from event MON87705 that also contain these junction sequences are considered to be isolated or isolatable, whether these sequences are present within the genome of the cells of event MON87705 or present in detectable amounts in tissues, progeny, biological samples or commodity products derived from the event MON87705.

A DNA molecule of the present invention may also be a recombinant DNA molecule. As used herein, the term recombinant means any agent (e.g. DNA, peptide etc.), that is, or results, however indirect, from human manipulation of a nucleic acid molecule.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from soybean event MON87705 whether from a soybean plant or from a sample that includes DNA from the event. Probes according to the present invention include not only deoxyribonucleic or ribonucleic acids but also polyamides and other probe materials that bind specifically to a target DNA sequence and such binding can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 15 nucleotides or more, more preferably 18 nucleotides or more, more preferably 20 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization*, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a embodiment, a nucleic acid of the present invention will specifically hybridize to one or more of the nucleic acid molecules set forth in SEQ ID NO: 1 and 2 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1 and SEQ ID NO: 2 or complements or fragments of either under high stringency conditions. In one aspect of the present invention, a marker nucleic acid molecule of the present invention has the nucleic acid sequence set forth in SEQ ID NO: 1 and SEQ ID NO: 2 or complements thereof or fragments of either. In another aspect of the present invention, a marker nucleic acid molecule of the present invention shares 80%, 81%, 82%, 83%, 84%, 85%, 86%, 87%, 88%, 89%, 90%, 912%, 92%, 93%, 94%, 95%, 96%, 97%, 98%, 99% and 100% sequence identity with the nucleic acid sequence set forth in SEQ ID NO: 1 and SEQ ID NO: 2 or complement thereof or fragments of either. In a further aspect of the present invention, a marker nucleic acid molecule of the present invention shares 95% 96%, 97%, 98%, 99% and 100% sequence identity with the sequence set forth in SEQ ID NO: 1 and SEQ ID NO: 2 or complement thereof or fragments of either. SEQ ID NO: 1 and SEQ ID NO: 2 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY; all of which is herein incorporated by reference. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA molecule, this distance can range from one nucleotide base pair up to about twenty thousand nucleotide base pairs. The use of the term "amplicon" specifically excludes primer-dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from soybean event MON87705 with seed samples deposited as ATCC PTA-9241 can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that results in the production of a fluorescent signal. The fluorescent signal indicates the presence of the flanking/transgene insert sequence due to successful amplification and hybridization.

Other described methods, such as microfluidics (US Patent Pub. 2006068398, U.S. Pat. No. 6,544,734) provide methods and devices to separate and amplify DNA samples. Optical dyes are used to detect and quantitate specific DNA molecules (WO/05017181). Nanotube devices (WO/06024023) that comprise an electronic sensor for the detection of DNA molecules or nanobeads that bind specific DNA molecules and can then be detected.

Figure 2:
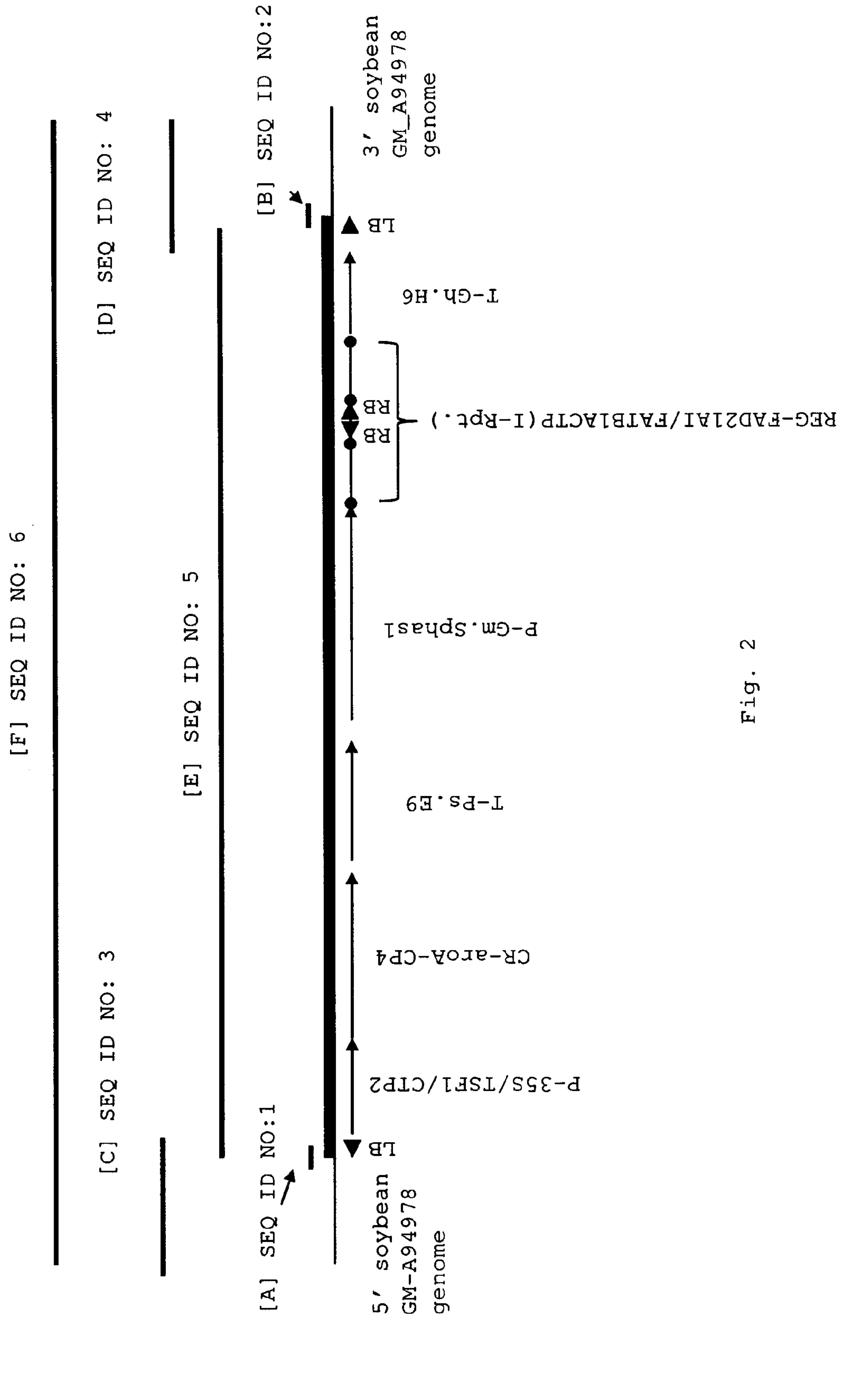
FIG. 2. Organization of the transgenic insert in the genome of soybean event MON87705; [A] corresponds to the relative position of SEQ ID NO: 1 which forms the junction between SEQ ID NO: 3 and SEQ ID NO: 5; [B] corresponds to the relative position of SEQ ID NO: 2 which forms the junction between SEQ ID NO: 4 and SEQ ID NO: 5; [C] corresponds to the relative position of SEQ ID NO: 3, the soybean genome sequence flanking the arbitrarily assigned/designated 5' end of the expression cassette integrated into the genome in event MON87705; [D] corresponds to the relative position of SEQ ID NO: 4, the soybean genome sequence flanking the arbitrarily assigned/designated 3' end of the expression cassette integrated into the genome in event MON87705; [E] represents the various elements comprising SEQ ID NO: 5 and is the sequence of the expression cassette inserted into the genome of the event MON87705; and [F] represents the contiguous sequence comprising, as represented in the figure from left to right, SEQ ID NO:3, SEQ ID NO:5 and SEQ ID NO:4, in which SEQ ID NO:1 and SEQ ID NO:2 are incorporated as set forth above, as these sequences are present in the genome in event MON87705.

DNA detection kits can be developed using the compositions disclosed herein and the methods well known in the art of DNA detection. The kits are useful for the identification of soybean event MON87705 DNA in a sample and can be applied to methods for breeding soybean plants containing the appropriate event DNA. The kits may contain DNA primers or probes that are homologous or complementary to SEQ ID NO: 1 through SEQ ID NO: 5 or DNA primers or probes homologous or complementary to DNA contained in the transgene genetic elements of DNA. These DNA sequences can be used in DNA amplification reactions or as probes in a DNA hybridization method. The sequences of the genomic DNA and transgene genetic elements contained in MON87705 soybean genome are illustrated in FIG. 2; the transgene genetic element contained in the T-DNAs are organized as follows: the first T-DNA begins with the octopine left border sequence, followed by the first artificial gene comprised of the 35S enhancer from figwort mosaic virus (FMV), and promoter, intron, and leader sequence from the *Arabidopsis thaliana* Tsfl gene, which is upstream of the ShkG transit peptide fused to an optimized aroA-CP4, which is upstream of the 3' UTR of the RbcS2 (E9) gene from *Pisum sativum*, followed by the second cassette which is comprised of the promoter and leader sequence from the *Glycine max* 7S alpha prime subunit of beta-conglycinin gene, which is upstream of the sense half of the inverted repeat containing sequences homologous to the *Glycine max* FAD2 and FATB genes, which is upstream of the nopaline right border sequence. The second T-DNA begins with the nopaline right border sequence, which is upstream of the antisense half of the inverted repeat containing sequences homologous to the *Glycine max* FAD2 and FATB genes, which is upstream of the 3' UTR of the *Gossypium barbadense* (Sea island cotton) H6 gene, which is upstream of the octopine left border sequence. The primer molecules derived from these sequences can be used as part of a primer set that also includes a DNA primer molecule derived from the genome flanking the transgene insert of event MON87705 as presented in SEQ ID NO: 3 and SEQ ID NO: 4.

The present invention includes a soybean plant comprising a DNA molecule comprising a polynucleotide having a sequence that is or is complementary to a sequence selected from the group consisting of SEQ ID NOs: 1, 2 and 18. In another aspect, the present invention includes a soybean plant part, where the plant part comprises a polynucleotide having a sequence that is or is complementary to a sequence selected from the group consisting of SEQ ID NOs: 1, 2 and 18. In another aspect, the present invention includes progeny of a soybean plant, where the progeny comprises a polynucleotide having a sequence that is or is complementary to a sequence selected from the group consisting of SEQ ID NOs: 1, 2 and 18.

The present invention also includes a soybean plant capable of producing seeds having an oil composition comprising approx. 55-80% oleic acid and less than 8% saturated fatty acid, wherein genetic determinants for said oil composition is obtainable from soybean having ATCC Accession No. PTA-9241. In another aspect, the present invention includes a method for producing a soybean plant comprising altered fatty acid levels, comprising crossing a plant comprising soybean event MON87705 with a soybean plant lacking soybean event MON87705 to obtain a plant comprising said soybean event MON87705 and altered fatty acid levels, wherein a representative sample of seed comprising said event was deposited under ATCC Accession No. PTA-9241. In a further aspect, the present invention also includes a method of producing a soybean variety comprising soybean event MON87705, comprising backcrossing soybean event MON87769 into said variety, wherein a representative sample of seed comprising said event was deposited under ATCC Accession No. PTA-9241.

The present invention also includes an oil composition obtained from seeds comprising a DNA molecule comprising a polynucleotide having a sequence that is or is complementary to a sequence selected from the group consisting of SEQ ID NOs: 1, 2 and 18. In another aspect, the present invention includes a commodity product derived from an oil composition selected from the group consisting of cooking oil, salad oil, shortening, lecithin, nontoxic plastics, printing inks, lubricants, waxes, hydraulic fluids, electric transformer fluids, solvents, cosmetics, hair care products and biodiesel.

The present invention also includes a DNA molecule comprising a polynucleotide having a sequence that is or is complementary to one selected from the group consisting of sequences listed under SEQ ID NOs: 1, 2 and 18. In another aspect, the present invention includes an isolated DNA molecule comprising at least from about 11 to about 20 consecutive nucleotides selected from the group consisting of SEQ ID NO: 1 and SEQ ID NO: 2.

The present invention also includes a genome of a soybean cell comprising a polynucleotide having a sequence selected from the group consisting of sequences listed under SEQ ID NOs: 1, 2 and 18.

In another aspect, the present invention includes a method of detecting the presence of soybean event MON87705 DNA in a biological sample comprising contacting the sample with a probe that hybridizes under stringent hybridization conditions with a sequence selected from the group consisting of SEQ ID NO: 1 and SEQ ID NO: 2, and their complements, and does not hybridize under stringent hybridization conditions with soybean plant genomic DNA that that does not comprise a sequence selected from the group consisting of SEQ ID NO: 1 and SEQ ID NO: 2, and their complements; subjecting the sample and probe to stringent hybridization conditions; and detecting binding of the probe to the sample; where binding is diagnostic for the presence of said DNA in the sample.

In another aspect, the present invention includes a method for detecting the presence of a nucleotide sequence diagnostic for the presence of soybean event MON87705 in a biological sample, comprising detecting the presence of a nucleotide sequence wherein said sequence is selected from the group consisting of SEQ ID NOs: 1, 2 and 18, wherein said biological sample is selected from the group consisting of soybean meal, soy flour, soy protein concentrate, soy protein isolates, texturized soy protein concentrate, hydrolyzed soy protein and whipped topping.

The present invention also includes a kit for detecting the presence or absence of soybean transgenic event MON87705 in a soybean sample comprising nucleotide components designed based on detecting one or more sequences shown under SEQ ID NOs: 1, 2 and 18. In another aspect, the present invention also includes a composition having a DNA molecule selected from the group consisting of SEQ ID NOs: 1, 2 and 18, wherein said composition is a commodity product selected from the group consisting of soybean meal, soy flour, soy protein concentrate, soy protein isolates, texturized soy protein concentrate, hydrolyzed soy protein and whipped topping.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Soybean A3525 with pMON95829 and Event Selection

The transgenic soybean plant MON87705 was generated by an *Agrobacterium*-mediated transformation of soybean cells with DNA fragments derived from pMON95829 (FIG. 1). The binary plant transformation vector, pMON95829 contains two plant transformation T-DNAs. Each T-DNA was flanked by right border (RB) and left border (LB) sequences at the ends of the T-DNAs. Post transformation screening of MON87705 identified a right border to right border co-integration of the two T-DNAs generating a two cassette insertion, one designed to express the aroA-CP4 gene from *Agrobacterium tumefaciens* imparting glyphosate tolerance and the other designed with an inverted repeat to trigger the RNAi based suppression of the endogenous FAD2 and FATB genes (SEQ ID NO: 7). The inverted repeat structure is not found in pMON95829, but is formed with a RB to RB co-integration of the two T-DNAs. This integration configuration yields a single transgenic locus containing both expression and suppression cassettes and is flanked by residual left border sequences (FIG. 2). The unique sequence generated at the RB:RB integration site is listed under SEQ ID NO: 18.

The T-DNAs are organized as follows: the first T-DNA begins with the octopine LB sequence, followed by the first artificial gene comprised of the 35S enhancer from figwort mosaic virus (FMV) and the promoter, intron, and leader sequence from the *Arabidopsis thaliana* Tsfl gene, which is upstream of the ShkG transit peptide fused to an optimized aroA-CP4, which is upstream of the 3' UTR of the RbcS2 (E9) gene from *Pisum sativum*, followed by the second cassette which is comprised of the promoter and leader sequence from the *Glycine max* 7S alpha prime subunit of beta-conglycinin gene, which is upstream of the sense half of the inverted repeat containing sequences homologous to the *Glycine max* FAD2 and FATB genes, which is upstream of the nopaline RB sequence. The second T-DNA begins with the nopaline RB sequence, which is upstream of the antisense half of the inverted repeat containing sequences homologous to the *Glycine max* FAD2 and FATB genes, which is upstream of the 3' UTR of the *Gossypium barbadense* (Sea island cotton) H6 gene, which is upstream of the octopine LB sequence.

Explants transformed with pMON95829 were obtained via *Agrobacterium tumefaciens*-mediated transformation. Plants were regenerated from transformed tissue. Approximately 955 R0 transformation events were produced and were tested for the presence of the two T-DNAs by Invader' (Third Wave Technologies, Inc., Madison, Wis.). In addition, a PCR designed to identify the RB:RB configuration was used to select properly-assembled candidate events. R0 events demonstrating the proper co-integration of the T-DNAs were self-pollinated to generate R1 seed. The fatty acid composition of the R1 seed was determined by FAME-GC analysis. Based on these analyses, 48 events were carried forward to the R2 generation. Segregation of multi copy events and phenotypic characterization narrow the candidate event pool to 11 events by the R3 generation.

Detailed southern analysis designed to verify copy number, cassette intactness, locus and absence of undesired vector sequence was performed. In subsequent generations, field performance characteristics, as well as sequence flanking the insertion site for the remaining events, were also determined. One progeny line designated event MON87705 was selected based upon its overall fatty acid composition profile (Table 1), agronomic performance and molecular characteristics.

TABLE 1

| Fatty Acid Composition Profile (weight % of total fatty acids) | | | | | |
|---|---|---|---|---|---|
| Soy Line | 16:0 | 18:0 | 18:1 | 18:2 | 18:3 |
| Wild type | 12.2 | 4.2 | 19.0 | 54.9 | 8.0 |
| MON87705 | 2.5 | 3.4 | 72.8 | 12.3 | 7.4 |

Example 2

Isolation of Flanking Sequences Using Inverse PCR

Sequences flanking the T-DNA insertion in MON87705 were determined using inverse PCR as described in Ochman et al., 1990 (PCR Protocols: A guide to Methods and Applications, Academic Press, Inc.) and by TAIL (Thermal Asymmetric InterLaced) PCR. Plant genomic DNA was isolated from both wild-type A3525 and the transgenic line from tissue grown under green house conditions. Frozen leaf tissue was ground by mortar and pestle with liquid nitrogen or mechanical grinding. A volume of 22 mL of extraction buffer was added to ~1 g of ground leaf tissue and incubated at 65° C. for 1 hour. The CTAB extraction buffer consisted of 1.4M NaCl, 2% CTAB, 20 mM EDTA, and 100 mM Tris-HCl pH 8.0. Just prior to use, 0.02% beta-mercaptoethanol and 0.5 mg RNase A was added to the extraction buffer. The samples were extracted with 12 mL of phenol/chloroform/isoamyl alcohol (25:24:1) solution and then centrifuged at 4000×G for 10 minutes at 4° C. The supernatant was transferred to a new tube and the DNA was precipitated with 15 mL of isopropanol. After centrifugation at 4000×G for 10 minutes, the pellets were washed with 5 mL 70% ethanol. A final centrifugation at 4000×G for 5 minutes was performed; the pellets were air dried and then re-suspended in 300 μL of water.

An aliquot of DNA was subjected to TAIL PCR and a region of sequence adjacent to the insertion site was isolated and sequenced. Additionally an aliquot of DNA was digested with restriction endonucleases selected based upon restriction analysis of the T-DNA. After self-ligation of restriction fragments, PCR was performed using primers designed from the T-DNA sequence that would amplify sequences extending away from the 5' and 3' ends of the T-DNA. PCR products were separated by agarose gel electrophoresis and purified using a QIAGEN gel purification kit (Qiagen, Valencia, Calif.). The subsequent products were sequenced directly using standard sequencing protocols.

Extension of the initial flanking sequence extending away from the 5' end of the T-DNA was performed using the Genomewalker™ kit (Clontech, Mountain View, Calif.). Standard protocol conditions were used and primers presented as SEQ ID NO: 19 and SEQ ID No: 20 were used in the nested PCR along with the supplied AP1 and AP2 primers. Reactions were run in duplicate and products were cloned and sequenced directly using standard sequencing protocols. Sequences were compared to the duplicate run, prior genomic sequences, and the 3' flanking sequence to determine actual polymorphisms from PCR-derived errors. There is apparently a chromosomal duplication that occurred upon generation of the MON87705 event. This region of duplication (SEQ ID NO: 17) corresponds to position 1053 through 3422 of SEQ ID NO: 6 and is nearly identical to position 10682 through 13051 of SEQ ID NO: 6. We have determined that there are two polymorphisms between the repeat located on the 5' end of the insert and the repeat from the 3' end of the insert, with the 3' end of the insert matching the original genomic sequence.

Using these methods, the identified 5' flanking sequence of the insertion was presented as SEQ ID NO: 3 (see FIG. 2), and the 3' flanking sequence was presented as SEQ ID NO: 4 (see FIG. 2). The portion of the inserted cassettes (SEQ ID NO: 7) from pMON95829 that was fully integrated into the A3525 genomic DNA is presented as SEQ ID NO: 5 (see FIG. 2).

Isolated sequences were compared to the T-DNA sequence to identify the flanking sequence and the co-isolated T-DNA fragment. Confirmation of the presence of the expression cassette was achieved by PCR with primers designed based upon the deduced flanking sequence data and the known T-DNA sequence. The A3525 wild type sequence corresponding to the same region in which the T-DNA was integrated in the transformed line was isolated using primers designed from the flanking sequences in MON87705. The flanking sequences in MON87705 and the A3525 wild type sequence were analyzed against multiple nucleotide and protein databases. This information was used to examine the relationship of the transgene to the plant genome and to look at the insertion site integrity. The flanking sequence and wild type sequences were used to design primers for TaqMan endpoint assays used to identify the events and determine zygosity as described in Example 3.

Example 3

Event-specific Endpoint TaqMan and Zygosity Assays

The methods used to identify event MON87705 in a sample are event-specific endpoint TaqMan PCR assays for which examples of conditions are described in Table 2 and Table 3. The first set of DNA primers that may be used in the endpoint assays are primers SQ20129 (SEQ ID NO: 8), SQ20130 (SEQ ID NO: 9) and 6FAM™ labeled primer PB10043 (SEQ ID NO: 10). The second set of DNA primers that may be used in the endpoint assays are primers SQ21928 (SEQ ID NO:11), SQ20901 (SEQ ID NO:12), and 6FAM™ labeled primer PB10164 (SEQ ID NO:13). 6FAM™ is a fluorescent dye product of Applied Biosystems (Foster City, Calif.) attached to the DNA primers. For TaqMan MGB (Minor Groove Binding) probes, the 5'exonuclease activity of Taq DNA polymerase cleaves the probe from the 5'-end, between the fluorophore and quencher. When hybridized to the target DNA strand, quencher and fluorophore are separated enough to produce a fluorescent signal.

SQ20129 (SEQ ID NO: 8) and SQ20130 (SEQ ID NO: 9) when used as described with PB10043 (SEQ ID NO: 10) produce a DNA amplicon that is diagnostic for event MON87705 DNA. SQ21928 (SEQ ID NO: 11) and SQ20901 (SEQ ID NO: 12) when used as described with PB10164 (SEQ ID NO: 13) produce a DNA amplicon that is also diagnostic for event MON87705 DNA. The controls for these analyses should include a positive control from soybean known to contain event MON87705 DNA, a negative control from non-transgenic soybean and a negative control that contains no template DNA. Similar assays can be designed for SEQ ID 18

These assays are optimized for use with an Applied Biosystems GeneAmp PCR System 9700, Stratagene Robocycler, MJ Engine, Perkin-Elmer 9700 or Eppendorf Mastercycler Gradient thermocycler. Other methods and apparatus may be known to those skilled in the art to produce amplicons that identify the event MON87705 DNA.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 2

Soybean MON87705 Event Specific Endpoint TaqMan PCR Assay

| Step | Reagent | Volume | Comments |
|---|---|---|---|
| 1 | 18 megohm water | adjust for final volume of 10 μl | |
| 2 | 2X Universal Master Mix | 5 μl | 1X final concentration of buffer |
| 3 | Event Primer-SQ20129 and SQ20130 Mix (or event primer SQ21928 and SQ20901) (resuspended in 18 megohm water to a concentration of 20 μM for each primer)<br>Example: In a microcentrifuge tube, the following should be added to achieve 500 μl at a final concentration of 20 μM:<br>100 μl of Primer 1 at a concentration of 100 μM<br>100 μl of Primer 2 at a concentration of 100 μM<br>300 μl of 18 megohm water | 0.5 μl | 1.0 μM final concentration |
| 4 | Event 6-FAM ™ Probe PB10043 or PB10164 (resuspended in 18 megohm water to a concentration of 10 μM)<br>Note: 6-FAM ™ Probe is light sensitive. | 0.2 μl | 0.2 μM final concentration |
| 5 | Internal Control Primer-SQ1532, SQ1533 Mix (resuspended in 18 megohm water to a concentration of 20 μM for each primer) | 0.5 μl | 1.0 μM final concentration |
| 6 | Internal Control VIC ™ Probe PB359 (resuspended in 18 megohm water to a concentration of 10 μM)<br>Note: VIC ™ Probe is light sensitive. | 0.2 μl | 0.2 μM final concentration |
| 7 | Extracted DNA (template):<br>Leaf Samples to be analyzed<br>Negative control (non-transgenic DNA)<br>Negative water control (No template control)<br>Positive control GM_A94978 DNA | 3.0 μl | |

TABLE 3

Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds<br>64° C. 1 minute<br>−1° C./cycle |
| 30 | 95° C. 15 seconds<br>54° C. 1 minute |
| 1 | 10° C. Forever |

Determining zygosity for event MON87705 in a sample was done using an event-specific zygosity endpoint TaqMan PCR assay for which examples of conditions are described in Table 4 and Table 5. The DNA primers used in the zygosity assay are primers SQ20901 (SEQ ID NO: 12), SQ21928 (SEQ ID NO: 11), SQ21905 (SEQ ID NO: 15), 6FAM™ labeled primer PB10164 (SEQ ID NO: 13) and VIC™ labeled primer PB10335 (SEQ ID NO: 14). 6FAM™ and VIC™ are fluorescent dye products of Applied Biosystems (Foster City, Calif.) attached to the DNA primers.

SQ20901 (SEQ ID NO: 12) and SQ21928 (SEQ ID NO: 11) when used in these reaction methods with PB10164 (SEQ ID NO: 13) produce a DNA amplicon that is diagnostic for event MON87705 DNA. The controls for this analysis should include a positive control from soybean containing event MON87705 DNA, a negative control from non-transgenic soybean and a negative control that contains no template DNA. SQ21928 (SEQ ID NO: 11) and SQ21905 (SEQ ID NO: 15) when used in these reaction methods with PB10335 (SEQ ID NO: 14) produce a DNA amplicon that is diagnostic for the wild type allele and contains SEQ ID NO: 16 in its entirety. Heterozygosity is determined by the presence of both amplicons demonstrated by the liberation of fluorescent signal from both probes PB10164 and PB10335.

These assays are optimized for use with an Applied Biosystems GeneAmp PCR System 9700, Stratagene Robocycler, MJ Engine, Perkin-Elmer 9700 or Eppendorf Mastercycler Gradient thermocycler. Other methods and apparatus known to those skilled in the art that produce amplicons that identify the event MON87705 DNA is within the skill of the art.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 4

Soybean MON87705 Event-Specific Zygosity Endpoint TaqMan PCR

| Step | Reagent | Volume | Comments |
|---|---|---|---|
| 1 | 18 megohm water | adjust for final volume of 10 μl | |
| 2 | 2X Universal Master Mix | 5 μl | 1X final concentration |
| 3 | Zygosity primer - SQ20901, SQ21928, SQ21905 (resuspended in 18 megohm water to a concentration of 20 μm for each primer)<br>Example: In a microcentrifuge tube, the following should be added to achieve 500 μl at a final concentration of 20 μM:<br>100 μl of each primer at a concentration of 100 μM<br>200 μl of 18 megohm water | 0.5 μl | 1 μM final concentration |
| 4 | Event 6-FAM ™ Probe (PB10164) (resuspended in 18 megohm water to a concentration of 10 μM) | 0.2 μl | 0.20 μM final concentration |

TABLE 4-continued

Soybean MON87705 Event-Specific Zygosity Endpoint TaqMan PCR

| Step | Reagent | Volume | Comments |
|---|---|---|---|
| | Note: 6-FAM ™ Probe is light sensitive. | | |
| 5 | Wild Type VIC ™ Probe (PB10335) (resuspended in 18 megohm water to a concentration of 10 μM)<br>Note: VIC ™ Probe is light sensitive. | 0.2 μl | 0.20 μM final concentration |
| 6 | Extracted DNA (template):<br>Leaf Samples to be analyzed<br>Negative control (non-transgenic DNA)<br>Negative water control (No template control)<br>Positive control Homozygous GM_A94978 DNA<br>Positive control Hemizygous GM_A94978 DNA | 3.0 μl | |

TABLE 5

Zygosity Endpoint TaqMan thermocycler conditions

| Cycle No. | Settings |
|---|---|
| 1 | 50° C. 2 minutes |
| 1 | 95° C. 10 minutes |
| 10 | 95° C. 15 seconds<br>64° C. 1 minute<br>−1° C./cycle |
| 30 | 95° C. 15 seconds<br>54° C. 1 minute |
| 1 | 10° C. Forever |

Example 4

Identification of Event MON87705 in a Given Soybean Sample

The following example describes how one may identify the presence or absence of MON87705 event in a given soybean sample.

DNA event primer pairs are used to produce an amplicon diagnostic for soybean event MON87705. An amplicon diagnostic for MON87705 comprises at least one junction sequence: SEQ ID NO: 1, SEQ ID NO: 2 or SEQ ID NO: 18. SEQ ID NO: 1 (FIG. 2) is a nucleotide sequence corresponding to the junction of the 5' flanking sequence (positions 3413 through 3422 of SEQ ID NO: 6, see FIG. 2) and the integrated border of the insertion (positions 3423 through 3433 of SEQ ID NO: 6, see FIG. 2). SEQ ID NO: 2 (see FIG. 2) is a nucleotide sequence corresponding to the junction of the integrated border of the insertion (positions 10664 through 10673 of SEQ ID NO: 6, see FIG. 2) and the 3' flanking sequence (positions 10674 through 10683 of SEQ ID NO: 6, see FIG. 2). SEQ ID NO: 18 is a nucleotide sequence corresponding to the right border to right border junction (positions 9230 to 9335 of SEQ ID NO: 6) generated upon the cointegration of the two pMON95829 T-DNAs to yield event MON87705

Event primer pairs that will produce a diagnostic amplicon for MON87705 include primer pairs based upon the flanking sequences and the inserted cassettes. To acquire a diagnostic amplicon in which at least 11 nucleotides of SEQ ID NO: 1 is found, one would design a forward primer based upon SEQ ID NO: 3 from bases 1 through 3448 and a reverse primer based upon the inserted cassette, SEQ ID NO: 5 from positions 10 through 7251. To acquire a diagnostic amplicon in which at least 11 nucleotides of SEQ ID NO: 2 is found, one would design a forward primer based upon the inserted cassette, SEQ ID NO: 5, from positions 1 through 7241 and a reverse primer based upon the 3' flanking sequence, SEQ ID NO: 4, from bases 10 through 2515. For practical purposes, one should design primers which produce amplicons of a limited size range, preferably between 200 to 1000 bases. Smaller sized amplicons in general are more reliably produced in PCR reactions, allow for shorter cycle times and can be easily separated and visualized on agarose gels or adapted for use in endpoint TaqMan-like assays. In addition, amplicons produced using said primer pairs can be cloned into vectors, propagated, isolated and sequenced or can be sequenced directly with methods well established in the art. Any primer pair derived from the combination of SEQ ID NO: 3 and SEQ ID NO: 5 or the combination of SEQ ID NO: 4 and SEQ ID NO: 5 that are useful in a DNA amplification method to produce an amplicon diagnostic for MON87705 or progeny thereof is an aspect of the present invention. Any single isolated DNA polynucleotide primer molecule comprising at least 11 contiguous nucleotides of SEQ ID NO: 3, or its complement that is useful in a DNA amplification method to produce an amplicon diagnostic for MON87705 or progeny thereof is an aspect of the present invention. Any single isolated DNA polynucleotide primer molecule comprising at least 11 contiguous nucleotides of SEQ ID NO: 4, or its complement that is useful in a DNA amplification method to produce an amplicon diagnostic for MON87705 or progeny thereof is an aspect of the present invention. Any single isolated DNA polynucleotide primer molecule comprising at least 11 contiguous nucleotides of SEQ ID NO: 5, or its complement that is useful in a DNA amplification method to produce an amplicon diagnostic for MON87705 or progeny thereof is an aspect of the present invention.

An example of the amplification conditions for this analysis is illustrated in Table 6 and Table 7. However, any modification of these methods or the use of DNA primers homologous or complementary to SEQ ID NO: 3 or SEQ ID NO: 4 or DNA sequences of the genetic elements contained in the transgene insert (SEQ ID NO: 5) of MON87705 that produce an amplicon diagnostic for MON87705, is within the art. A diagnostic amplicon comprises a DNA molecule homologous or complementary to at least one transgene/genomic junction DNA listed under SEQ ID NO: 1, 2 and 18, or a substantial portion thereof.

An analysis for event MON87705 plant tissue sample should include a positive tissue control from event MON87705, a negative control from a soybean plant that is not event MON87705, for example, but not limited to A3525, and a negative control that contains no soybean genomic DNA. A primer pair that will amplify an endogenous soybean DNA molecule will serve as an internal control for the DNA amplification conditions. Additional primer sequences can be selected from SEQ ID NO: 3, SEQ ID NO: 4, or SEQ ID NO: 5 by those skilled in the art of DNA amplification methods, and conditions selected for the production of an amplicon by the methods shown in Table 6 and Table 7 may differ, but result in an amplicon diagnostic for event MON87705 DNA. The use of these DNA primer sequences with modifications to the methods of Table 6 and Table 7 are within the scope of the invention. The amplicon produced by at least one DNA primer sequence derived from SEQ ID NO: 3, SEQ ID NO: 4 or SEQ ID NO: 5 that is diagnostic for MON87705 is an aspect of the invention.

DNA detection kits that contain at least one DNA primer derived from SEQ ID NO: 3, SEQ ID NO: 4 or SEQ ID NO: 5, that when used in a DNA amplification method, produces a diagnostic amplicon for MON87705 or its progeny is an aspect of the invention. A soybean plant or seed, wherein its genome will produce an amplicon diagnostic for MON87705 when tested in a DNA amplification method is an aspect of the invention. The assay for the MON87705 amplicon can be performed by using an Applied Biosystems GeneAmp PCR System 9700, Stratagene Robocycler, MJ Engine, Perkin-Elmer 9700 or Eppendorf Mastercycler Gradient thermocycler or any other amplification system that can be used to produce an amplicon diagnostic of MON87705 as shown in Table 7.

TABLE 6

Soybean MON87705 Event Specific PCR Assay

| Step | Reagent | Volume | Comments |
|---|---|---|---|
| 1 | 18 megohm water | adjust for final volume of 10 ul | |
| 2 | 2X Universal Master Mix (Contains dNTPs, enzyme and buffer) | 5.0 ul | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer 1 at a concentration of 100 uM 100 ul of Primer 2 at a concentration of 100 uM 300 ul of 18 megohm water | 0.5 ul | 1.0 uM final concentration |
| 5 | Extracted DNA (template) 50 ng of genomic DNA: Leaf samples to be analyzed Negative control (non-transgenic DNA) Negative water control (no template control) Positive control MON88769 DNA | 3.0 ul | |

TABLE 7

Soybean MON87705 Event Thermocycler Conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

A deposit of seeds of the soybean event MON87705 disclosed above and recited in the claims, has been made under the Budapest Treaty with the American Type Culture Collection (ATCC), 10801 University Boulevard, Manassas, Va. 20110. The ATCC accession number is PTA-9241. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

We claim:

1. A method for producing a soybean plant seed comprising crossing a plant comprising soybean event MON87705 with a soybean plant lacking soybean event MON87705 to obtain a progeny plant seed comprising said soybean event MON87705, wherein a representative sample of seed comprising said event was deposited under ATCC Accession No. PTA-9241, wherein a plant grown from said progeny plant seed is capable of producing seeds having an oil composition comprising between 55-80% oleic acid and less than 8% saturated fatty acid.

2. The method of claim 1, further comprising backcrossing a soybean plant comprising soybean event MON87769 with a plant grown from said progeny plant seed to produce a backcross progeny plant seed, wherein a representative sample of seed comprising soybean event MON87769 was deposited under ATCC Accession No. PTA-8911.

3. The method of claim 1, further comprising detecting said soybean event MON87705 in said progeny plant seed or a plant grown from said progeny plant seed, wherein said detecting soybean event MON87705 comprises detecting soybean event MON87705 DNA in a DNA sample of said progeny plant seed or a plant grown from said progeny plant seed, wherein said detecting soybean event MON87705 DNA in a DNA sample comprises:

i. contacting the DNA sample with a probe that hybridizes under stringent hybridization conditions with a sequence selected from the group consisting of SEQ ID NO: 1, SEQ ID NO: 2, SEQ ID NO: 18, and their complements, and does not hybridize under stringent hybridization conditions with soybean plant genomic DNA that does not comprise a sequence selected from the group consisting of SEQ ID NO: 1, SEQ ID NO: 2, SEQ ID NO: 18, and their complements;

ii. subjecting the DNA sample and probe to stringent hybridization conditions; and iii. detecting binding of the probe to the DNA sample;

wherein binding is diagnostic for the presence of soybean event MON87705 DNA in the DNA sample.

4. The method of claim 1, wherein said soybean plant lacking soybean event MON87705 is a MON87705-deficient soybean variety.

5. The method of claim 4, wherein said cross is an out-cross.

6. The method of claim 5, further comprising growing said progeny plant seed having said soybean event MON87705, backcrossing said grown progeny plant to said soybean plant variety, and selecting a backcross progeny seed or plant having said soybean event MON87705.

7. The method of claim 6, further comprising selfing said backcross progeny plant one or more times to prepare a variety adapted to specific local growing conditions.

8. The method of claim 7, further comprising detecting said soybean event MON87705 in said variety adapted to specific growing conditions, wherein said detecting soybean event MON87705 comprises detecting soybean event MON87705 DNA in a DNA sample of said variety adapted to specific growing conditions, wherein said detecting soybean event MON87705 DNA in a DNA sample comprises:

i. contacting the DNA sample with a probe that hybridizes under stringent hybridization conditions with a sequence selected from the group consisting of SEQ ID NO: 1, SEQ ID NO: 2, SEQ ID NO: 18, and their complements, and does not hybridize under stringent hybridization conditions with soybean plant genomic DNA that does not comprise a sequence selected from the group consisting of SEQ ID NO: 1, SEQ ID NO: 2, SEQ ID NO: 18, and their complements;

ii. subjecting the DNA sample and probe to stringent hybridization conditions; and iii. detecting binding of the probe to the DNA sample;

wherein binding is diagnostic for the presence of soybean event MON87705 DNA in the DNA sample.

9. The method of claim 4, further comprising growing said progeny plant seed having said soybean event MON87705, backcrossing said grown progeny plant to said MON87705-deficient soybean variety, and selecting a backcross progeny seed or plant having said soybean event MON87705.

10. The method of claim 6, further comprising selfing said backcross progeny plant one or more times.

11. The method of claim 6, further comprising one or more additional backcrosses to said soybean plant variety to produce an additional backcross progeny plant.

12. The method of claim 11, further comprising selfing said additional backcross progeny plant.

13. The method of claim 2, further comprising selfing said backcross progeny plant one or more times.

14. A method of producing a hybrid seed comprising crossing a plant comprising soybean event MON87705 with a second soybean plant to obtain a progeny plant seed comprising said soybean event MON87705, wherein a representative sample of seed comprising said event was deposited under ATTC Accession No. PTA-9241.

15. The method of claim 14, wherein said plant comprising soybean event MON87705 is homozygous for said soybean event MON87705.

16. The method of claim 14, wherein said second soybean plant comprises soybean event MON87705.

17. The method of claim 16, wherein said second soybean plant is homozygous for said soybean event MON87705.

* * * * *